(12) United States Patent
Zhou et al.

(10) Patent No.: US 9,108,995 B2
(45) Date of Patent: Aug. 18, 2015

(54) SPIROBENZYLAMINE-PHOSPHINE, PREPARATION METHOD THEREFOR AND USE THEREOF

(75) Inventors: Qilin Zhou, Tianjin (CN); Shoufei Zhu, Tianjin (CN); Yanbo Yu, Tianjin (CN); Kun Li, Tianjin (CN); Lixin Wang, Tianjin (CN)

(73) Assignee: Zhejiang Jiuzhou Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 14/240,918

(22) PCT Filed: Jul. 27, 2012

(86) PCT No.: PCT/CN2012/079257
§ 371 (c)(1),
(2), (4) Date: Feb. 25, 2014

(87) PCT Pub. No.: WO2013/029446
PCT Pub. Date: Mar. 7, 2013

(65) Prior Publication Data
US 2014/0194638 A1 Jul. 10, 2014

(30) Foreign Application Priority Data
Aug. 31, 2011 (CN) .......................... 2011 1 0252000

(51) Int. Cl.
| | | |
|---|---|---|
| C07F 9/50 | (2006.01) | |
| C07F 15/00 | (2006.01) | |
| C07B 35/02 | (2006.01) | |
| C07B 53/00 | (2006.01) | |
| C07C 51/36 | (2006.01) | |
| B01J 31/18 | (2006.01) | |

(52) U.S. Cl.
CPC ............. *C07F 15/004* (2013.01); *B01J 31/189* (2013.01); *C07B 35/02* (2013.01); *C07B 53/00* (2013.01); *C07C 51/36* (2013.01); *C07F 9/505* (2013.01); *C07F 9/5022* (2013.01); *C07F 15/0033* (2013.01); *B01J 2231/645* (2013.01); *B01J 2531/827* (2013.01); *C07B 2200/07* (2013.01)

(58) Field of Classification Search
USPC .......................................... 556/13, 20, 21, 26
See application file for complete search history.

(56) References Cited

U.S. PATENT DOCUMENTS

2011/0118472 A1* 5/2011 Zhou et al. .................... 548/101

FOREIGN PATENT DOCUMENTS

| CN | 1884290 | 12/2006 |
|---|---|---|
| CN | 101565434 | 12/2006 |
| CN | 101565434 | 10/2009 |
| CN | 101671365 | 3/2010 |
| CN | 102040625 | 5/2011 |
| CN | 102391306 | 3/2012 |
| EP | 2272853 | 1/2011 |
| JP | 2011518788 | 6/2011 |

OTHER PUBLICATIONS

International Search Report; dated Nov. 8, 2012; International Application No. PCT/CN2012/079257; International Filing Date: Jul. 27, 2012; 4 pages.
English translation; International Search Report; dated Nov. 8, 2012; International Application No. PCT/CN2012/079257; International Filing Date: Jul. 27, 2012; 3 pages.
Angewandte Chemie Internationai Editon, Jul. 12, 2011, vol. 50, No. 32, pp. 7329-7332, see schemes 2-3 and table 1.
Xie et al; "Chiral Iridium Spiro Aminophosphine Complexes: Asymmetric Hydrogenation of Simple Ketones, Structure, and Plausible Mechanism"; Chemistry an Asian Journal, 2011, vol. 6, pp. 899-908 (11 pages).
Zhu et al.; "Well-Defined Chiral Spiro Iridium/Phosphine-Oxazoline Cationic Complexes for Highly Enantioselective Hydrogenation of Imines at Ambient Pressure", JACS Articles; J.AM.CHEM.SOC. 2006, vol. 128, pp. 12886-12891 (7 pages).
English abstract dated Mar. 17, 2010; Chinese Application No. CN101671365 ; 1 page.
English abstract dated May 4, 2011; Chinese Application No. CN102040625 ; 1 page.
English abstract; Chinese Application No. CN102391306 dated Mar. 28, 2012; 1 page.

(Continued)

*Primary Examiner* — Sudhakar Katakam
*Assistant Examiner* — Pancham Bakshi
(74) *Attorney, Agent, or Firm* — Blank Rome LLP

(57) ABSTRACT

The present invention relates to a spirobenzylamine-phosphine, preparation method therefor and use thereof. The compound has a structure represented by formula (I), wherein n=0 to 3; $R^1$, $R^2$, $R^3$, $R^4$, $R^5$, $R^6$, $R^7$, $R^8$ and $R^9$ having a value as defined in claim 1. Starting from the substituted 7-trifluoromesyloxy-7'-diarylphosphino-1,1'-spiro-dihydroindene, the compound is synthesized in a two-step or three-step reactions. The new spirobenzylamine-phosphine is complexed with an iridium precursor and is subjected to ion exchange, to give an Iridium/spirobenzylamine-phosphine complex comprising various anions. The spiro benzyl amine-phosphine/Iridium complex according to the present invention may be used for catalyzing asymmetry hydrogenation of a variety of alpha-substituted acrylic acids, has high activity and enantioselectivity, and has a good prospect of industrialization.

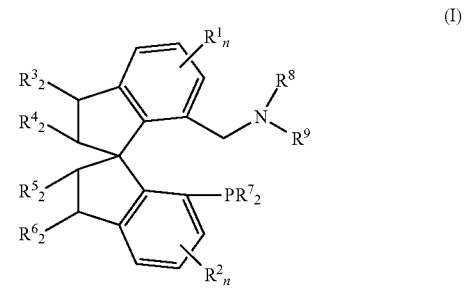

(I)

5 Claims, No Drawings

(56) References Cited

OTHER PUBLICATIONS

English abstract dated Oct. 28, 2009; Chinese Application No. CN101565434 1 page.
English abstract dated Dec. 27, 2006; Chinese Application No. CN1884290; 1 page.
English abstract dated Jun. 30, 2011; Japanese Application No. JP2011518788; 1 page.
English translation of claims dated Jun. 9, 2015; Japanese Application No. JP2011518788; 4 pages.

European Search Report dated Mar. 31, 2015 related to corresponding European Application No. 12828043.5; 6 pages.
Shoufei, Zhu; "Studies on synthesis of chiral spiro monophosphoramidites and phosphino-nitrogen lignands and the application thereof;" Nan Kai University China; pp. 81-82; completed May 1, 2005.
Xie, Jian Hua et al., An Additional Coordination Group Leads to Extremely Efficient Chiral Iridium Catalysts for Asymmetric Hydrogenation of Ketones, Angewandte Chemie, International Edition, Jul. 12, 2011, vol. 50, No. 32, pp. 7329-7332, see schemes 2-3 and table 1.

\* cited by examiner

SPIROBENZYLAMINE-PHOSPHINE, PREPARATION METHOD THEREFOR AND USE THEREOF

REFERENCE TO RELATED APPLICATION

The present application is a national stage of PCT/CN2012/079257, filed Jul. 27, 2012, which claims priority of Chinese patent application No. 201110252000.7, filed on Aug. 31, 2011, titled "Spirobenzylamine-phosphine, preparation method therefor and use thereof", the entire contents of which are hereby incorporated by reference.

FIELD OF THE INVENTION

The present invention relates to a new spirobenzylamine-phosphine, synthesis method therefor and application thereof. This invention particularly introduce the method to synthesize the new spirobenzylamine-phosphine mentioned above from the raw material of substituted 7-trifluoromesyloxy-7'-diarylphosphino-1,1'-spiro-dihydroindene by a two-step or three-step reaction. The new spirobenzylamine-phosphine is complexed with an iridium precursor and is subjected to ion exchange, to give an iridium/spirobenzylamine-phosphine complex comprising various anions. The new Iridium complex of spiro benzyl amine-phosphine may be used in asymmetric hydrogenation of a variety of alpha-substituted acrylic acids, in which the reaction activity is very high and enantioselectivity and has a good prospect of industrialization.

BACKGROUND OF THE INVENTION

Transition-metal-catalyzed asymmetric synthesis is an important area in modern organic chemistry study (Ohkuma, T; Kitamura, M.; Noyori, R. Catalytic Asymmetry Synthesis, Wiley, New York, 2000). The crux of the asymmetric catalytic synthesis is to synthesize the chiral catalyst. Since the asymmetric control emerged by chiral catalyst which depends on chiral ligands, for the core of the synthesis of chiral catalyst is the synthesis of chiral ligands. The motivation of the asymmetric synthesis development is to design and synthesize the new chiral ligands.

Chiral carboxylic acid, one of the important blocks for synthesis, is widely applied into synthesis of drugs and nature products. Wherein alpha-aryl substituted propionic acid, such as naproxen and ibuprofen, is widespread used in the world today as a non-steroidal anti-inflammatory drug. There is significant application value to develop the synthesis method of optical active alpha-substituted propionic acids with high efficiency and high selectivity. To obtain the compound, transition-metal-catalyzed asymmetric hydrogenation of alpha-substituted acrylic acids is one of the most direct and effective method. In the past several decades, much research on transition-metal-catalyzed asymmetric hydrogenation of alpha-substituted acrylic acids has been done and some valid chiral ligands and catalysts are developed. Among the research of asymmetric hydrogenation of alpha-substituted acrylic acids so far, axial chiral diphosphine ligands and the complex catalyst of ruthenium acquire the best results. Nevertheless, to maximize the catalytic effect for such catalyst requires hydrogen pressure greater than 6 MPa in general. If hydrogen pressure is reduced, the activity and enantioselectivity of reaction is lowered (1. Ohta, T.; Takaya, H.; Kitamura, M.; Nagai, K.; Noyori, R. J. Org. Chem. 1987, 52, 3174; 2. Chan, A. S. C.; Laneman, S. A. U.S. Pat. No. 5,144,050, 1992; 3. Benincori, T.; Brenna, E.; Sannicolò, F.; Trimarco, L.; Antognazza, P.; Cesarotti, E.; Demartin, F.; Pilati, T. J. Org. Chem. 1996, 61, 6244; 4. Pai, C.-C.; Lin, C.-W.; Lin, C.-C.; Chen, C.-C.; Chan, A. S. C. J. Am. Chem. Soc. 2000, 122, 11513; 5. Qiu, L.; Wu, J.; Chan, S.; Au-Yeung, T. T.-L.; Ji, J.-X.; Guo, R.; Pai, C.-C.; Zhou, Z.; Li, X.; Fan, Q.-H.; Chan, A. S. C. Proc. Natl. Acad. Sci. U.S.A. 2004, 101, 5815). The reaction condition of high pressure has a high requirement of apparatus and causes many security problems in production. Diphosphine ligands and complex catalyst of rhodium are also used in asymmetric hydrogenation alpha-substituted acrylic acids. Although some rhodium catalysts have relatively high enantioselectivity in asymmetric hydrogenation alpha-substituted acrylic acids, the catalyst dosage is large (1 mol %) and the enantioselectivity in substrates of alpha-alkyl substituted acrylic acids is only middle class which is not adequate enough (1. Robin, F.; Mercier, F.; Ricard, L.; Mathey, F.; Spagnol, M. Chem. Eur. J. 1997, 3, 1365; 2. Hu, W.-H.; Pai, C. C.; Chen, C. C.; Xue, G.-P.; Chan, A. S. C. Tetrahedron: Asymmetry 1998, 9, 3241; 3. Zupančič, B.; Mohar, B.; Stephan, M. Org. Lett. 2010, 12, 3022). Recently, some phosphine-oxazoline ligand and complex of iridium are used to catalyze the asymmetric hydrogenation of alpha-substituted acrylic acids. However, since the conversion number (TON<100) and transformation frequency (TOF<13 h$^{-1}$) is relative low and the highest enantioselectivity is only 88% ee, the requirement of practical application can not be fulfilled (1. Scrivanti, A.; Bovo, S.; Ciappa, A.; Matteoli, U. Tetrahedron Lett. 2006, 47, 9261; 2. Zhang, Y.; Han, Z.-B.; Li, F.-Y.; Ding, K.-L.; Zhang, A. Chem. Commun. 2010, 46, 156). In conclusion, with regard to asymmetric hydrogenation alpha-substituted acrylic acids, the existing chiral ligands and catalysts have defects of high hydrogen pressure, large catalyst dosage, long duration of reaction and limited substrates, which have negative effect on practical application. Therefore, to overcome the shortages of existing ligands and catalysts is one of the focuses of the research to develop new effective chiral ligand and corresponding catalyst.

SUMMARY OF THE INVENTION

The objective of the present invention is to provide a spirobenzylamine-phosphine, synthesis method therefor and uses thereof, capable of overcoming the defects of the existing technique. The new spiro benzyl amine-phosphine/iridium complex may be used in asymmetric catalytic hydrogenation of a variety of alpha-substituted acrylic acids, having a high activity, enantioselectivity and good prospect of industrialization.

The spirobenzylamine-phosphine compound provided here is a compound having a structure of formula (I).

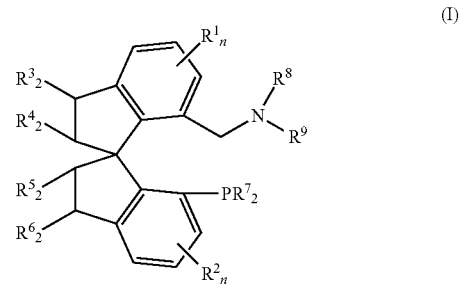

Wherein: n=0~3; $R^1$ and $R^2$ represent $C_1$-$C_8$ alkyl, halogenated alkyl, $C_1$-$C_8$ alkoxy, $C_2$-$C_8$ acyloxy, $C_1$-$C_8$ acyl, $C_2$-$C_8$ ester group, ($C_1$-$C_8$ acyl) azyl, ($C_1$-$C_8$ alkyl)diamino group, halogen, phenyl, substituted phenyl, naphthyl, substituted naphthyl, furyl, thienyl, and fused aliphatic ring or fused aromatic ring when n≥2; $R^1$ and $R^2$ can be either identical or not;

$R^3$, $R^4$, $R^5$ and $R^6$ represent H, $C_1$-$C_8$ alkyl, halogenated alkyl, $C_1$-$C_8$ alkoxy, $C_2$-$C_8$ acyloxy, $C_1$-$C_8$ acyl, $C_2$-$C_8$ ester group, ($C_1$-$C_8$ acyl) azyl, ($C_1$-$C_8$ alkyl)diamino group, halogen, phenyl, substituted phenyl, naphthyl, substituted naphthyl, furyl and thienyl; $R^3$-$R^4$, $R^5$-$R^6$ may be fused aliphatic ring or aromatic ring. $R^3$, $R^4$, $R^5$ and $R^6$ can be either identical or not;

$R^7$ represents $C_1$-$C_8$ alkyl, phenyl, substituted phenyl, naphthyl, substituted naphthyl, furyl, and thienyl;

$R^8$ and $R^9$ represent H, $C_1$-$C_8$ alkyl, benzyl, substituted benzyl, phenyl, substituted phenyl, naphthyl, substituted naphthyl, furyl and thienyl; R8 and R9 can be either identical or not;

In the substituted phenyl or naphthyl described above, the substituent groups may be one or more of $C_1$-$C_8$ alkyl, $C_1$-$C_8$ alkoxy, hydroxyl, $C_2$-$C_8$ acyloxy, halogen, amino, ($C_1$-$C_8$ acyl) azyl, ($C_1$-$C_8$ alkyl)diamino group, $C_1$-$C_8$ acyl and $C_2$-$C_8$ ester group; The number of substituent ranges from 0 to 5.

In the spirobenzylamine-phosphine (I) described in the present invention:

$C_1$-$C_8$ alkyl described above can be methyl, ethyl, propyl, isopropyl, butyl, isobutyl sec-butyl, tert-butyl, pentyl, isopentyl, neopentyl, sec-pentyl, tert-pentyl, hexyl, isohexyl, neohexyl, sec-hexyl, tert-hexyl, heptyl, isoheptyl, neoheptyl, sec-heptyl, tert-heptyl, octyl, isooctyl, neooctyl, sec-octyl or tert-octyl.

$C_1$-$C_8$ alkoxy described above can be methoxy, ethoxy, n-propoxy, isopropoxy, n-butoxy, isobutoxy, sec-butoxy, tert-butoxy, n-pentyloxy, isopentyl, neopentyl, sec-pentyloxy, tert-pentyloxy, n-hexyloxy, isohexyloxy, neohexyloxy, sec-hexyloxy, tert-hexyloxy, n-heptyloxy, isoheptyloxy, neoheptyloxy, sec-heptyloxy, tert-heptyloxy, n-octyloxy, iso-octyloxy, neooctyloxy, sec-octyloxy or a tert-octyloxy;

$C_1$-$C_8$ acyl described above can be formyl, acetyl, propionyl, n-butyryl, isobutyryl, n-valeryl, isovaleryl, sec-valeryl, pivaloyl, n-hexanoyl, isohexanoyl, neohexanoyl, sec-hexanoyl n-heptanoyl,
isoheptanoyl, neoheptanoyl, sec-heptanoyl, n-caprylyl, isocaprylyl, neocaprylyl, sec-caprylyl, 1-cyclopropylformyl, 1-cyclobutylformyl, 1-cyclopentylformyl, 1-cyclohexylformyl, 1-cycloheptylformyl;

$C_2$-$C_8$ acyloxy described above can be acetoxy, propionyloxy, n-butyryloxy, isobutyryloxy, n-valeryloxy, isovaleryloxy, neovaleryloxy sec-valeryloxy, n-hexanoyloxy, isohexanoyloxy, neohexanoyloxy, sec-hexanoyloxy, n-heptanoyloxy, isoheptanoyloxy, neoheptanoyloxy, sec-heptanoyloxy, n-octanoyloxy, isooctanoyloxy, neooctanoyloxy, sec-octanoyloxy, 1-cyclopropylformyloxy, 1-cyclobutyl formyloxy, 1-cyclopentylformyloxy, 1-cyclohexylformyloxy, 1-cycloheptylformyloxy;

$C_2$-$C_8$ ester group described above can be methoxycarbonyl, ethoxycarbonyl, propoxycarbonyl, isopropoxycarbonyl, butyloxycarbonyl, isobutyloxycarbonyl, n-pentyloxycarbonyl, isopentyloxycarbonyl, neopentyloxycarbonyl, sec-pentyloxycarbonyl, tert-pentyloxycarbonyl, cyclopentyloxycarbonyl, n-hexyloxycarbonyl, isohexyloxycarbonyl, neohexyloxycarbonyl, sec-hexyloxycarbonyl, tert-hexyloxycarbonyl, cyclohexyloxycarbonyl, n-heptyloxycarbonyl, iso-heptyloxycarbonyl, neoheptyloxycarbonyl, sec-heptyloxycarbonyl, tert-heptyloxycarbonyl, cycloheptyloxycarbonyl.

The halogenated alkyl described above can be the ones containing fluorine, chlorine, bromine or iodine.

The spirobenzylamine-phosphine (I) described in the present invention also includes the raceme, dextroisomer, laevoisomer with the same chemical structure general formula but different stereochemical structure and optical activity.

The preparation method of spirobenzylamine-phosphine described in the present invention includes the following steps:

Firstly, the substituted 7-trifluoromesyloxy-7'-diarylphosphino-1,1'-spiro-dihydroindene is subjected as the raw material in the palladium-catalyzed cyanation reaction to prepare the intermediate 2;

Secondly, the spirobenzylamine-phosphine 3 wherein $R^8$ and $R^9$ are both H is given by the reacting cyano compound 2 by reductant;

The amino group of spirobenzylamine-phosphine 3 is subjected to a substitution reaction to prepare other spirobenzylamine-phosphine wherein $R^8$ and $R^9$ are not both H.

The specific reaction is as follow:

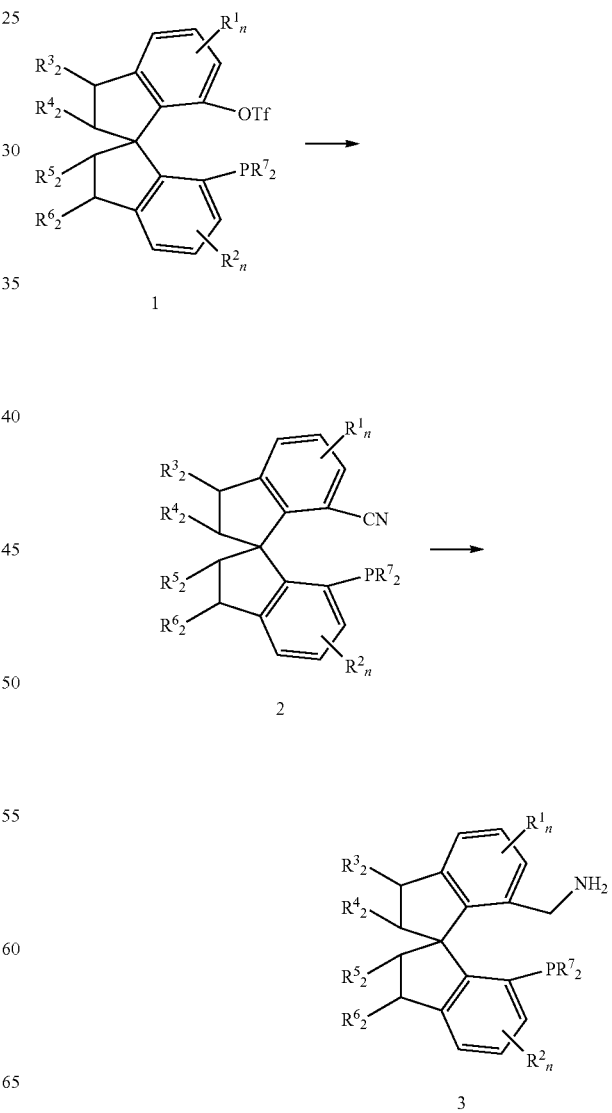

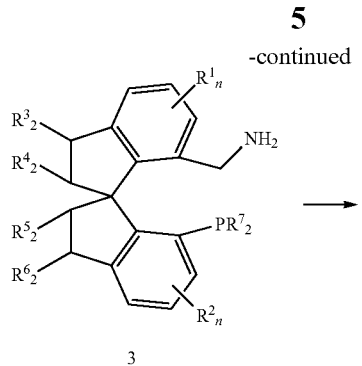

3

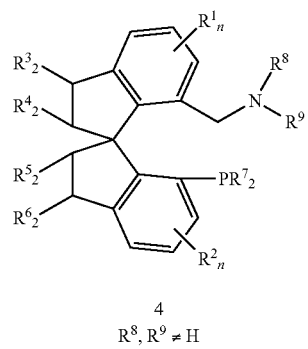

4
$R^8, R^9 \neq H$

Wherein n=0 to 3; Values of $R^1$, $R^2$, $R^3$, $R^4$, $R^5$, $R^6$, $R^7$, $R^8$ and $R^9$ are defined as compound (1) described above.

A type of Iridium complex of spiro benzyl amine-phosphine provided by the present invention, which is prepared by spirobenzylamine-phosphine, has the following structure formula:

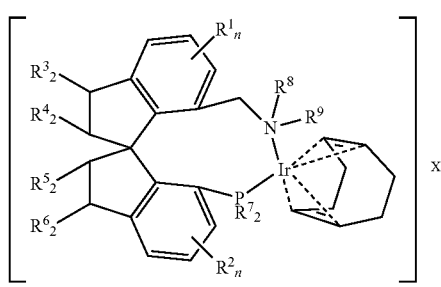

5

Wherein:

is cyclooctadiene; n=0 to 3; Values of $R^1$, $R^2$, $R^3$, $R^4$, $R^5$, $R^6$, $R^7$, $R^8$ and $R^9$ are defined as Claim 1; X represents halogen, $C_1$-$C_8$ carboxylate, sulfate, tetrakis[3,5-bis(trifluoromethyl)phenyl]borate, tetrakis(pentafluorphenyl)borate, tetra(perfluoro-tert-butoxyl)aluminate, tetrakis(hexafluoroisopropoxy)aluminate, hexafluorophosphate, hexafluoroantimonate, perchlorate, tetrafluoroborate, or trifluoromethanesulfonate.

The cyclooctadiene ligand may be replaced by ethylene and norbornadiene.

The Iridium complex of spiro benzyl amine-phosphine described above is prepared by the following steps: At the temperature of 10 to 50, spirobenzylamine-phosphine (1 mol) is reacted with monovalent iridium compound such as [Ir(COD)Cl]$_2$ (COD=cycloocatadiene) (0.5-1 mol) for 0.5 to 24 hours in organic solvent (one or several of dichloromethane, trichloromethane, 1,2-dichloroethane) to obtain the Iridium complex of spiro benzyl amine-phosphine with Cl as the anion. The Iridium complex of spiro benzyl amine-phosphine with various anions can be obtained by anion exchange:

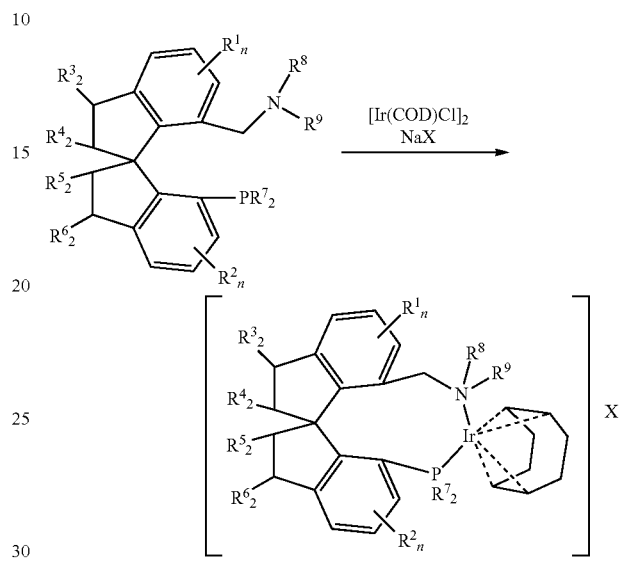

Wherein: n=0 to 3; Values of $R^1$, $R^2$, $R^3$, $R^4$, $R^5$, $R^6$, $R^7$, $R^8$ and $R^9$ and X are defined as Claim 6; COD represents 1,5-cyclooctadiene; The cycloocatadiene ligand may be replaced by ethylene and norbornadiene; sodium salt may be replaced by corresponding potassium salt, ammonium salt, silver salt and thallium salt.

The Iridium complex of spiro benzyl amine-phosphine can be applied into asymmetric catalytic hydrogenation of alpha-substituted acrylic acids.

$$R^{10} \overset{}{\underset{COOH}{\diagup\!\!\!\diagdown}} \xrightarrow[\text{Solvent}]{H_2/[Ir]/\text{additive}} R^{10} \overset{*}{\underset{COOH}{\diagup\!\!\!+\!\!\!\diagdown}}$$

Wherein: [Ir] represents the Iridium complex of spiro benzyl amine-phosphine described in Claim 6; $R^{10}$ represents $C_1$-$C_8$ alkyl, halogenated alkyl, benzyl, phenethyl, phenyl, substituted phenyl, naphthyl, substituted naphthyl, furyl and thienyl, $C_1$-$C_8$ alkoxy, benzyloxy, phenoxy; the atom starred is the chiral center.

Specific procedures: Catalyst and substrate are added into the inner pipe of reaction still. The Reaction still is sealed and replaced with hydrogen for 3 to 10 times after adding additive and solvent. The still is inflated with hydrogen to a certain pressure and the solution is stirred at a certain temperature until the reaction ends.

Conditions of catalyzed hydrogenation reaction described above: solvent used is $C_1$ to $C_6$ alcohol; catalyst dosage is 0.001-1 mol %; concentration of substrate is 0.001-10.0M; The additive consists of one or several of isopropamide, tert-butylamine, dimethylamine, diethylamine, diisopropylamine, disopropylethylamine, trimethylamine, triethylamine, 1,8-diazabicyclo[5.4.0]undec-7-ene, 1,4-diazabicyclo[2.2.2]octane, sodium hydride, sodium hydroxide, sodium carbonate, sodium bicarbonate, sodium tert-butoxide, potassium carbonate, potassium bicarbonate, potassium tert-butoxide, cesium hydroxide, cesium carbonate; The reaction temperature is 0-100; Hydrogen pressure is 0.1-10 MPa; reaction duration is 10 min-48 hours.

The present invention uses substituted 7-trifluoromesyloxy-7'-diarylphosphino-1,1'-spiro-dihydroindene as the raw material to synthesize the new spirobenzylamine-phosphine mentioned in the invention by a two-step or three-step reaction. The new spirobenzylamine-phosphine is complexed with an iridium precursor and is subjected to ion exchange, to give an Iridium complex spirobenzylamine-phosphine comprising various anions. The new Iridium complex of spiro benzyl amine-phosphine can catalyze asymmetric hydrogenation of various alpha-substituted acrylic acids and performs with the following feature: relatively low working pressure (generally 0.6 MPa), the asymmetric catalytic hydrogenation can be well performed even at normal pressure; wide range of application for substrates, the complex has considerable catalytic effect on both alpha-phenyl substituted acrylic acids and alpha-alkyl substituted acrylic acids; good functional group tolerance, the ester group, alkoxyl, aryloxy on the side chain are effect-less to the reaction result; high efficiency, transformation frequency may reach up to 6000 times/hour and the conversion number can be 10000; enantioselectivity can reach 99% ee. The features mentioned above indicates that the new Iridium complex of spiro benzyl amine-phosphine provided in the present invention have overcome the defects of the available technique and become one of the most efficient ligands and catalysts in asymmetric catalytic hydrogenation of alpha-substituted acrylic acids, owning a good prospect of industrialization.

DETAILED DESCRIPTION OF THE INVENTION

The present invention discloses the spirobenzylamine-phosphine, preparation methods and uses thereof. People skilled in the art can refer to the content in the invention and make reasonable adjustment to the technological parameters. It should be particularly noted that all of the similar replacement and modification which is obvious to one skilled in the art are treated as inclusion of the present invention. Since the method and application in the present invention has been described by particular examples with considerable results, relevant technicists are obviously incapable of adjusting and modifying the methods and application described in this article without referring to the content, spirits and scope of the present invention when attempting to realize and apply this technique.

The particular examples below can be helpful to comprehend the present invention. However, the protecting scope of the theme above should not be limited into the following examples. Instead, all the technique achieved based on this invention belong to the present invention.

Special Illustration:

The meanings of the contraction used in the particular examples are explained below:

Me represents methyl; Et represents ethyl; $^tBu$ represents tert butyl; ph represents phenyl; An represents p-methoxyphenyl; Xyl represents 3,5-dimethylphenyl; DTB represents 3,5-di-tert-butyl phenyl; $Bar_F$ represents tetrakis[3,5-bis(trifluoromethyl)phenyl]borate; OTf represents trifluoromethanesulfonate; $ClO_4$ represents perchlorate; $BF_4$ represents tetrafluoroborate; $PF_6$ represents hexafluorophosphate; DMF represents N,N-dimethylformamide; THF represents tetrahydrofuran; NMR is nuclear magnetic resonance; Chiral HPLC is high performance liquid chromatography with chiral chromatographic column; Chiral SFC is supercritical fluid chromatography; Chiral GC is gas chromatography with chiral capillary column; ee value is enantiomeric excess; S/C is the amount of substance ratio of substrate to catalyst mole.

All of the solvents involved are purified and dried by standard operation before applying into the preparation; the reagents involved are all commercially available or synthesized by methods in existing literature and purified before using.

Example 1

Preparation of (S)-7-cyano-7'-bis(3,5-di-tert-butylphenyl)phosphino-1,1'-spirobiinedane

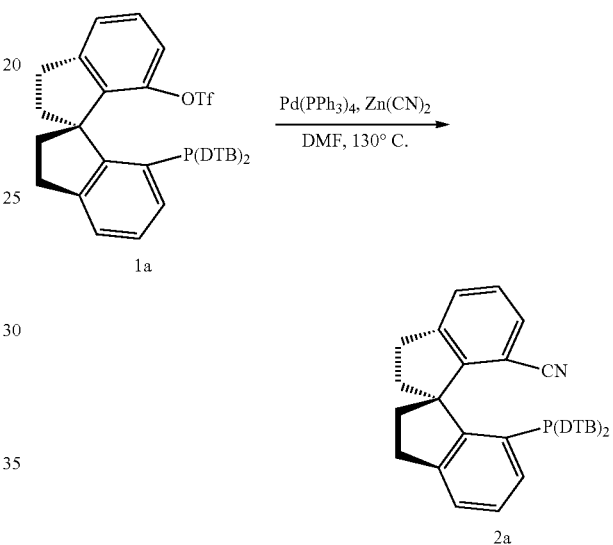

In nitrogen atmosphere, 4 mL DMF was added into a Schlenk flask containing (S)-1a (2.0 g, 2.6 mmol), tetrakis(triphenylphosphine)palladium (450 mg, 0.4 mmol) and zinc cyanide (610 mg, 5.2 mmol). The flask was heated to 160 and the reaction was processed with stirring for 3 days. The system was cooled to room temperature after the reaction ended and diluted by adding ethyl acetate. The mixture solution obtained was washed by saturated sodium carbonate aqueous solution and dried by anhydrous sodium sulfate. After the solvent was removed by rotary steaming, white solid 2a (1.5 g, 88%) was generated from the residue by column chromatography on silica gel (petroleum ether/dichloromethane). Melting point: 212-214. $[\alpha]_D^{30}$ −126 (c 0.5, $CH_2Cl_2$). $^1H$ NMR (400 MHz, $CDCl_3$) 7.41 (d, J=7.6 Hz, 1H, Ar—H), 7.31-7.30 (m, 2H, Ar—H), 7.24-7.20 (m, 2H, Ar—H), 7.09 (t, J=7.6 Hz, 1H, Ar—H), 7.03-7.00 (m, 1H, Ar—H), 6.94-6.88 (m, 3H, Ar—H), 6.78 (d, J=7.6 Hz, 2H, Ar—H), 3.21-3.03 (m, 4H, $CH_2$), 2.75-2.67 (m, 1H, $CH_2$), 2.43-2.35 (m, 3H, $CH_2$), 1.22 (s, 18H, $CH_3$), 1.16 (s, 18H, $CH_3$); $^{31}P$ NMR (162 MHz, $CDCl_3$) δ −16.9 (s); $^{13}C$ NMR (100 MHz, $CDCl_3$) δ 154.9, 153.8, 153.5, 150.4, 150.3, 150.2, 146.0, 144.6, 144.5, 138.2, 138.1, 135.5, 134.9, 133.7, 133.5, 131.3, 128.7, 128.1, 127.9, 127.4, 125.7, 122.7, 121.9, 117.3, 109.2, 63.0, 41.3, 40.0, 39.9, 35.2, 35.1, 31.8, 31.7, 31.3. HRMS (ESI) calcd for [M+H, $C_{46}H_{57}NP]^+$: 654.4223. Found 654.4230.

The compounds as follows were prepared by the same method as example 1.

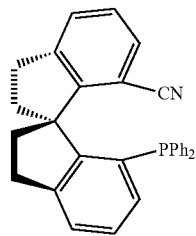

2b

It is white solid. Yield percentage: 89%. Melting point: 176-178; $[\alpha]^{20}_D$ -190 (c 1.05, CHCl$_3$); $^1$H NMR (300 MHz, CDCl$_3$) 7.42-6.92 (m, 16H, Ar—H), 3.16-3.05 (m, 4H, CH$_2$), 3.19-3.00 (m, 1H, CH$_2$), 2.55-2.32 (m, 3H, CH$_2$); $^{31}$P NMR (121 MHz, CDCl$_3$) -19.5 (s); $^{13}$C NMR (75 MHz, CDCl$_3$) 154.4, 153.8, 145.8, 144.8, 144.7, 138.7, 135.9, 134.8, 134.0, 133.8, 133.5, 133.3, 132.6, 132.3, 131.4, 128.8, 128.6, 128.4, 128.3, 127.3, 125.8, 127.3, 108.7, 62.8, 41.1, 39.7, 31.4, 31.0; HRMS (EI) calcd for C$_{30}$H$_{24}$NP: 429.1646. Found 429.1647.

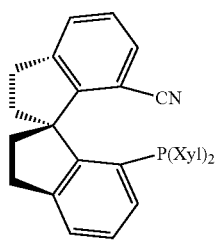

2c

It is white solid. Yield percentage: 88%. Melting point: 194-196

$[\alpha]_D^{30}$ -183 (c 0.5, CH$_2$Cl$_2$). $^1$H NMR (400 MHz, CDCl$_3$) 7.25 (d, J=7.6 Hz, 1H, Ar—H), 7.19-7.17 (m, 1H, Ar—H), 7.11-7.07 (m, 1H, Ar—H), 6.93-6.87 (m, 2H, Ar—H), 6.78-6.74 (m, 2H, Ar—H), 6.65 (d, J=7.6 Hz, 1H, Ar—H), 6.57-6.50 (m, 4H, Ar—H), 3.15-2.92 (m, 4H, CH$_2$), 2.77-2.69 (m, 1H, CH$_2$), 2.34-2.22 (m, 3H, CH$_2$), 2.10 (s, 6H, CH$_3$), 2.07 (s, 6H, CH$_3$); $^{31}$P NMR (162 MHz, CDCl$_3$) δ -20.1 (s); $^{13}$C NMR (100 MHz, CDCl$_3$) δ 153.1, 153.0, 152.2, 152.0, 144.6, 143.4, 143.3, 137.3, 137.2, 136.4, 136.2, 136.1, 133.6, 133.5, 131.9, 131.7, 130.9, 130.7, 130.0, 129.8, 129.7, 129.1, 128.8, 127.3, 126.8, 125.5, 124.3, 115.9, 107.6, 61.6, 40.2, 38.6, 30.3, 30.0, 29.9, 20.3, 20.2. HRMS (ESI) calcd for [M+H, C$_{34}$H$_{33}$NP]$^+$: 486.2345. Found 486.2345.

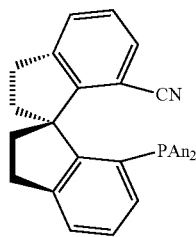

2d

It is white solid. Yield percentage: 90%. Melting point: 166-168. $[\alpha]_D^{23}$ -190 (c 0.5, CH$_2$Cl$_2$). $^1$H NMR (400 MHz, CDCl$_3$) δ 7.41 (d, J=7.3 Hz, 1H, Ar—H), 7.28 (d, J=7.3 Hz, 1H, Ar—H), 7.19 (t, J=7.4 Hz, 1H, Ar—H), 7.11 (t, J=7.5 Hz, 1H, Ar—H), 6.96 (m, 6H, Ar—H), 6.77 (d, J=8.0 Hz, 4H, Ar—H), 3.79 (s, 3H, CH$_3$), 3.76 (s, 3H, CH$_3$), 3.08 (m, 4H, CH$_2$), 2.58 (dd, J=21.6 and 10.2 Hz, 1H, CH$_2$), 2.34 (dd, J=17.5 and 9.4 Hz, 3H, CH$_2$). $^{31}$P NMR (162 MHz, CDCl$_3$) δ -23.8 (s); $^{13}$C NMR (100 MHz, CDCl$_3$): δ 170.3, 159.5, 159.3, 153.5, 152.4, 152.2, 145.0, 143.9, 143.8, 134.6, 134.4, 134.1, 133.5, 133.1, 132.9, 130.6, 128.9, 128.8, 128.1, 127.3, 126.7, 126.6, 126.5, 125.7, 124.9, 116.5, 113.5, 113.4, 113.3, 108.0, 62.1, 59.7, 54.6, 54.5, 40.4, 38.7, 38.6, 30.7, 30.3, 20.5, 13.8. HRMS (MALDI) calcd for [M+H, C$_{32}$H$_{28}$NO$_2$P]$^+$: 490.1933. Found 490.1922.

Example 2

Preparation of 7-aminomethyl-7'-bis(3,5-di-tert-butylphenyl)phosphino-1,1'-spirobiinedane

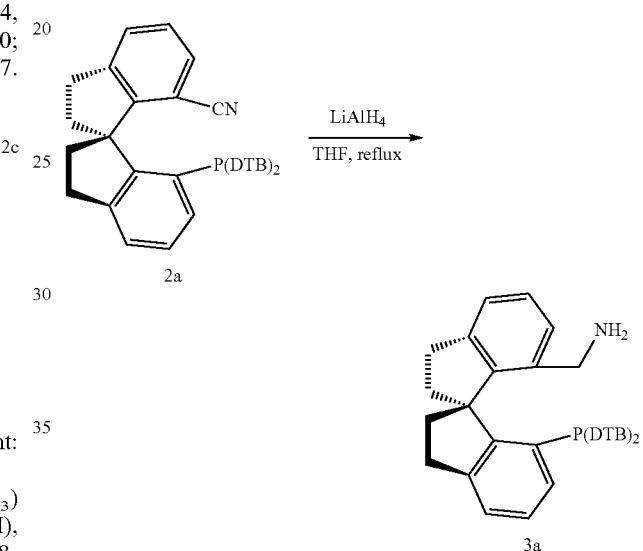

On cooling in ice water bath, tetrahydrofuran (20 mL) solution was slowly dripping into the turbid liquid formed by the mixing lithium aluminum hydride (304 g, 8 mmol) with 40 mL tetrahydrofuran. After dripping, the ice water bath was removed to make the mixture turn into room temperature naturally. The mixture was heating refluxed overnight and the terminal point of reaction was confirmed by TLC. The system was cooled to room temperature after the reaction ended and added with 40 mL water to quench the reaction. The tetrahydrofuran was removed by rotary steaming. The residue was diluted with ethyl acetate, washed by saturated sodium carbonate aqueous solution and saturated sodium chloride solution in turn and dried by anhydrous sodium sulfate. After the solvent was removed by rotary steaming, white foamed solid 3a (0.95 g, 94%) was generated from the residue by column chromatography on silica gel (petroleum ether/ethyl acetate=2:1, added with 2% triethylamine. Melting point: 112-114. $[\alpha]_D^{18}$ -162 (c 0.5, CH$_2$Cl$_2$). $^1$H NMR (400 MHz, CDCl$_3$) 7.25-7.00 (m, 7H, Ar—H), 6.87-6.77 (m, 3H, Ar—H), 6.58-6.56 (m, 2H, Ar—H), 3.16-2.86 (m, 6H, CH$_2$), 2.56-2.42 (m, 1H, CH$_2$), 2.22-2.03 (m, 3H, CH$_2$), 1.14 (s, 18H, CH$_3$), 1.04 (s, 18H, CH$_3$), 0.83 (brs, 2H, NH$_2$); $^{31}$P NMR (162 MHz, CDCl$_3$) δ -19.3 (s); $^{13}$C NMR (100 MHz, CDCl$_3$) δ 162.3, 155.6, 155.2, 150.2, 150.1, 149.9, 147.2, 147.1, 144.1, 143.2, 143.1, 139.1, 139.0, 135.4, 135.2, 134.7, 133.9, 133.7, 133.6, 133.3, 128.7, 128.5, 127.4, 127.3, 127.1, 126.7, 125.7, 124.8, 122.8, 122.6, 121.1, 62.8, 42.4, 40.4, 40.3, 38.9, 34.9, 34.8, 31.5, 31.4, 31.1, 30.9. HRMS (ESI) calcd for [M+H, C$_{46}$H$_{61}$NP]$^+$: 658.4536. Found 658.4530.

The compounds as follows were prepared by the same method as example 2.

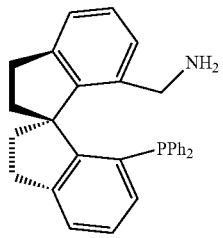

3b

It is white solid. Yield percentage: 90%. Melting point: 54-56. [α]$_D^{25}$ +186 (c 0.5, CH$_2$Cl$_2$). $^1$H NMR (400 MHz, CDCl$_3$) δ 7.32-7.28 (m, 2H, Ar—H), 7.24-7.02 (m, 11H, Ar—H), 6.95-6.91 (m, 2H, Ar—H), 6.86 (d, J=6.7 Hz, 1H, Ar—H), 3.19 (d, J=15.5 Hz, 1H, CH$_2$), 3.08-3.04 (m, 4H, CH$_2$), 2.87 (d, J=15.5 Hz, 1H, CH$_2$), 2.57-2.49 (m, 1H, CH$_2$), 2.34-2.26 (m, 2H, CH$_2$), 2.22-2.14 (m, 1H, CH$_2$), 1.26 (brs, 2H, NH$_2$); $^{31}$P NMR (162 MHz, CDCl$_3$) δ −22.0 (s); $^{13}$C NMR (100 MHz, CDCl$_3$) δ 155.7, 155.3, 147.2, 146.0, 145.7, 144.2, 144.1, 143.5, 143.4, 139.8, 139.6, 139.0, 136.1, 136.0, 134.7, 134.4, 132.9, 132.7, 132.0, 131.9, 131.7, 131.2, 130.9, 128.7, 128.2, 128.1, 128.0, 127.6, 127.3, 127.2, 125.9, 124.7, 122.8, 62.8, 42.3, 40.6, 40.5, 40.3, 39.5, 38.9, 31.0, 30.8, 29.7, 19.2. HRMS (ESI) calcd for [M+H, C$_{30}$H$_{29}$NP]$^+$: 434.2032. Found 434.2036.

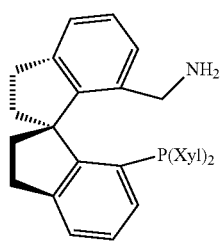

3c

It is white solid. Yield percentage: 92%. Melting point: 76-78. [α]$_D^{28}$ −216 (c 0.5, CH$_2$Cl$_2$). $^1$H NMR (400 MHz, CDCl$_3$) δ 7.23-7.12 (m, 5H, Ar—H), 6.90 (s, 1H, Ar—H), 6.83-6.79 (m, 2H, Ar—H), 6.65 (d, J=8.4 Hz, 2H, Ar—H), 6.56 (d, J=7.2 Hz, 2H, Ar—H), 3.16-2.97 (m, 5H, CH$_2$), 2.83-2.79 (d, J=15.6 Hz, 1H, CH$_2$), 2.68-2.60 (m, 1H, CH$_2$), 2.33-2.23 (m, 3H, CH$_2$), 2.21 (s, 6H, CH$_3$), 2.14 (s, 6H, CH$_3$), 0.89 (brs, 2H, NH$_2$); $^{31}$P NMR (162 MHz, CDCl$_3$) δ −21.7 (s); $^{13}$C NMR (100 MHz, CDCl$_3$) δ 155.4, 155.1, 147.3, 147.2, 144.2, 144.1, 143.2, 143.1, 139.5, 139.4, 139.1, 137.2, 137.1, 135.3, 135.1, 134.5, 134.4, 133.7, 133.4, 132.7, 132.5, 130.5, 130.3, 129.3, 127.0, 126.9, 125.6, 124.4, 122.6, 62.7, 62.6, 42.1, 40.5, 39.0, 31.1, 30.8, 21.3. HRMS (ESI) calcd for [M+H, C$_{34}$H$_{37}$NP]$^+$: 490.2658. Found 490.2660.

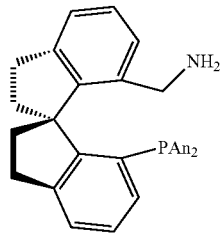

3d

It is white solid. Yield percentage: 92%. Melting point: 80-82. [α]$_D^{23}$ −131 (c 0.5, CH$_2$Cl$_2$). $^1$H NMR (400 MHz, CDCl$_3$) δ 7.10-6.93 (m, 4H, Ar—H), 6.92-6.82 (m, 3H, Ar—H), 6.82-6.69 (m, 3H, Ar—H), 6.63 (d, J=8.3 Hz, 2H, Ar—H), 6.57 (d, J=8.0 Hz, 2H, Ar—H), 3.57 (s, 3H, CH$_3$), 3.51 (s, 3H, CH$_3$), 3.07 (d, J=15.3 Hz, 1H, CH$_2$), 2.93-2.74 (m, 5H, CH$_2$), 2.42-2.27 (m, 1H, CH$_2$), 2.17-1.95 (m, 3H, CH$_2$), 0.83 (brs, 2H, NH$_2$); $^{31}$P NMR (162 MHz, CDCl$_3$) 6-25.2 (s); $^{13}$C NMR (100 MHz, CDCl$_3$) δ 159.7, 159.0, 154.6, 154.4, 146.6, 146.6, 143.6, 143.5, 142.9, 142.8, 138.7, 138.7, 135.5, 135.3, 134.0, 133.8, 133.7, 133.6, 133.5, 130.1, 123.0, 126.8, 126.7, 125.2, 124.4, 122.4, 113.4, 113.3, 113.3, 62.3, 62.2, 54.7, 54.6, 45.9, 41.9, 39.7, 39.7, 38.5, 30.6, 30.4. HRMS (MALDI) calcd for [M+H, C$_{32}$H$_{32}$NO$_2$P]$^+$: 494.2243.2658. Found 494.2237.

Example 3

Preparation of (S)—N-methyl-7-aminomethyl-7'-bis (3,5-di-tert-butylphenyl)phosphino-1,1'-spirobi-inedane

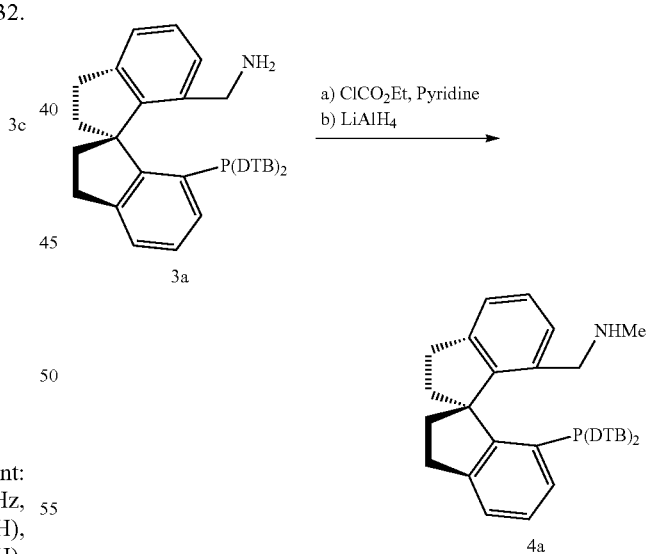

Under the protection of nitrogen, (S)-3a (100 mg, 0.15 mmol) and 2 mL anhydrous tetrahydrofuran were added into a Schlenk tube and the solids were completely dissolved by electromagnetic stirring. The temperature of the mixture was cooled to 0 in ice water bath. Anhydrous pridine (40 μL, 0.5 mmol) and ethyl chloroformate (20 mg, 0.18 mmol) was injected into the tube by syringe. The mixture turned to room temperature naturally and stirred overnight when reacting. After the reaction was confirmed to be ended by TLC, 6 mL ethyl acetate was added to dilute the system. After liquid separation, the organic phase was washed with 5% HCL and saturated sodium chloride solution in turn and dried by anhydrous sodium sulfate. The drying agent was removed by suction filtration while solvent was removed by pressure reduction. The solid obtained was dissolved by 2 mL dried tetrahydrofuran and cooled to around 0 in the ice water bath. Tetrahydrofuran solution was carefully added into the turbid liquid formed by mixing LiAlH$_4$ (27 mg, 0.7 mmol) with 2 mL tetrahydrofura. The mixture was heated to reflux in the oil bath. The reaction was processed with stirring overnight. After the reaction was confirmed to be ended by TLC, the oil bath was removed and replaced by ice water bath to cool the mixture. A small amount of water was added in order to quench the reaction. After diluted by 20 mL ethyl acetate and liquid separation, the organic layer was washed with 5% sodium hydroxide solution and saturated sodium chloride solution in turn, and was dried by anhydrous sodium hydride solution. After the solvent was removed by rotary steaming, white solid 4a (60 mg, 60%) was generated from the residue by column chromatography on silica gel (petroleum ether/ethyl acetate=20:1, added with 2% triethylamine). Melting point: 120-122. $[\alpha]_D^{25}$ −126 (c 0.5, CH$_2$Cl$_2$). $^1$H NMR (400 MHz, CDCl$_3$) δ 7.32-7.27 (m, 2H, Ar—H), 7.21-7.12 (m, 4H, Ar—H), 7.11-7.03 (m, 1H, Ar—H), 6.94-6.90 (m, 3H, Ar—H), 6.66 (dd, J=7.4 and 1.6 Hz, 2H, Ar—H), 3.13-0.92 (m, 5H, CH$_2$), 2.78 (d, J=13.5 Hz, 1H, CH$_2$), 2.42 (dd, J=21.9 and 11.2 Hz, 1H, CH$_2$), 2.29-2.22 (m, 3H, CH$_2$), 2.07 (s, 3H, CH$_3$), 1.21 (s, 18H, CH$_3$), 1.13 (s, 18H, CH$_3$), 1.02 (brs, 1H, NH). $^{31}$P NMR (162 MHz, CDCl$_3$) δ −18.9 (s). $^{13}$C NMR (100 MHz, CDCl$_3$) δ 155.5, 155.3, 149.9, 147.7, 144.0, 143.1, 138.7, 136.4, 135.4, 134.4, 133.5, 133.3, 128.5, 128.2, 127.3, 127.0, 126.6, 125.4, 122.9, 122.4, 121.1, 62.7, 52.3, 39.8, 39.1, 36.9, 34.7, 31.3, 30.8, 29.7. HRMS (ESI) calcd for [M+H, C$_{47}$H$_{73}$NP]$^+$: 672.4693. Found 672.4698.

Example 4

Preparation of (S)—N-benzyl-7-aminomethyl-7'-bis(3,5-di-tert-butylphenyl)phosphino-1,1'-spirobi-inedane

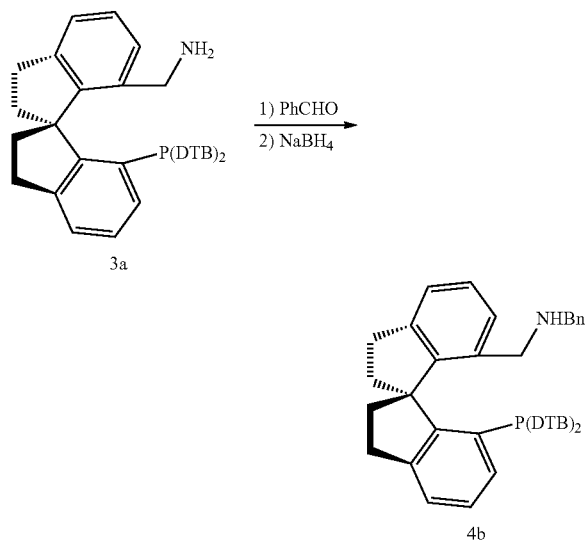

In nitrogen atmosphere, (S)-3a (250 mg, 0.38 mmol), 3 g 4 Å molecular sieve, benzaldehyde (39 µL, 0.38 mmol) and 10 mL dichloromethane were added into a Schlenk tube. At the temperature of 35, the mixture was stirred until the reaction completed. White solid was obtained after removing molecular sieve by suction filtration and removing solvent in vacuum. The white solid was added into a Schlenk tube before adding 10 mL methanol. The solid was dissolved with stirring. In nitrogen atmosphere, 300 mg of powdered sodium borohydride was added into the system stepwise on stirring until the reaction ended at room temperature. After adding 20 mL water to quench the reaction, the water phase was extracted by dichloromethane. The mixture was dried by anhydrous potassium carbonate. After the solvent was removed, white solid 4b (28 mg, 82%) was generated from the residue by column chromatography on silica gel (petroleum ether/ethyl acetate=16:1, added with 2% triethylamine). Melting point: 78-80. $[\alpha]_D^{23}$ −157 (c 0.5, CH$_2$Cl$_2$). $^1$H NMR (400 MHz, CDCl$_3$) δ 7.29 (s, 1H, Ar—H), 7.25-7.11 (m, 8H, Ar—H), 7.08 (m, 3H, Ar—H), 6.98-6.86 (m, 3H, Ar—H), 6.67 (d, J=6.5 Hz, 2H, Ar—H), 3.55 (d, J=13.3 Hz, 1H, CH$_2$), 3.32 (d, J=13.3 Hz, 1H, CH$_2$), 3.11 (d, J=13.2 Hz, 1H, CH$_2$), 2.99 (m, 3H, CH$_2$), 2.80 (m, 2H, CH$_2$), 2.45 (dd, J=21.9 and 10.4 Hz, 1H, CH$_2$), 2.23 m, 3H, CH$_2$), 1.55 (brs, 1H, NH), 1.20 (s, 18H), 1.13 (s, 18H). $^1$P NMR (162 MHz, CDCl$_3$) δ −19.1 (s). $^{13}$C NMR (100 MHz, CDCl$_3$) δ 155.6, 155.3, 149.8, 148.3, 144.1, 143.2, 140.6, 138.8, 136.4, 135.5, 134.4, 133.3, 128.4, 128.2, 127.9, 127.2, 126.5, 125.5, 123.0, 122.3, 121.1, 62.7, 53.9, 49.6, 40.0, 39.0, 34.7, 31.3, 30.9, 30.8, 29.7. HRMS (MALDI) calcd for [M+H, C$_{53}$H$_{66}$NP]$^+$: 748.5006. Found 748.5000.

Example 5

Preparation of Iridium Complex of Spiro Benzyl Amine-Phosphine

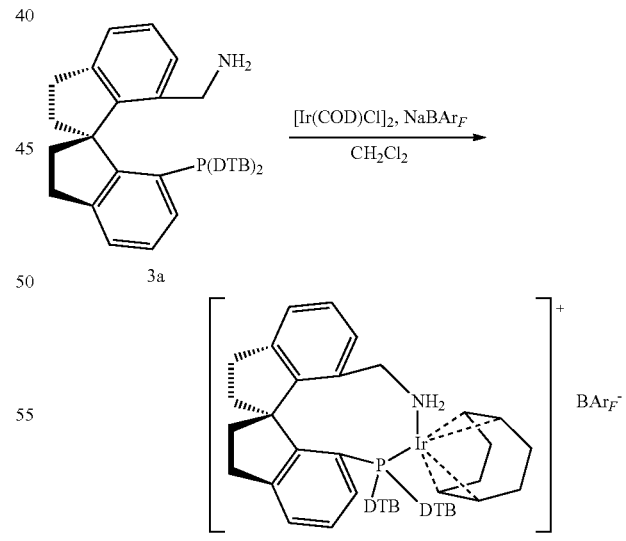

(S)-3a (56 mg, 0.085 mmol), [Ir(COD)Cl]$_2$ (32 mg, 0.047 mmol) and NaBAr$_F$ (100 mg, 0.107 mmol) were added into 10 mL Schlenk reaction flask before the newly steamed dichloromethane (2 mL) was injected into the flask with syringe. With the inspection of TLC, the reaction was processed for 2 hours with stirring and heating in the water bath. The system was stopped heating and cooled to room temperature after the complexation of ligands completed. After the solvent was removed, 5a (142 mg, 91%) was generated from the residue by column chromatography. The product was croci foamed solid. Melting point: 200-202. $[\alpha]_D^{25}$ +112 (c 0.5, $CH_2Cl_2$). $^1$H NMR (400 MHz, $CDCl_3$): δ 7.91 (d, J=6.3 Hz, 1H), 7.84-7.65 (m, 10H), 7.61 (s, 1H), 7.55-7.41 (m, 6H), 7.42-7.26 (m, 5H), 6.54 (m, 1H), 4.70 (dd, J=13.2 and 8.2 Hz, 1H), 4.15-4.00 (m, 1H), 3.72-3.62 (m, 1H), 3.58-3.54 (m, 1H), 3.49-3.44 (m, 1H), 3.41-3.35 (m, 1H), 3.02 (t, J=8.8 Hz, 2H), 2.84-2.80 (m, 1H), 2.74-2.59 (m, 2H), 2.44-2.35 (m, 1H), 2.07-2.03 (m, 2H), 1.94 (dd, J=16.6 and 9.7 Hz, 2H), 1.61-1.55 (m, 3H), 1.20 (s, 36H), 0.91-0.80 (m, 4H); $^{31}$P NMR (162 MHz, $CDCl_3$) δ 14.4 (s); $^{13}$C NMR (100 MHz, $CDCl_3$) δ 162.5, 162.0, 161.5, 161.0, 152.5, 151.7, 146.9, 146.6, 144.8, 134.8, 134.1, 132.5, 132.0, 130.9, 129.8, 129.5, 129.2, 128.6, 128.0, 127.8, 127.2, 126.7, 125.9, 124.0, 123.7, 123.2, 120.5, 119.2, 117.5, 73.7, 71.5, 70.3, 63.4, 61.5, 61.3, 47.2, 40.0, 34.9, 32.5, 31.0, 30.6, 30.2, 29.7, 29.1. HRMS (MALDI) calcd for $C_{54}H_{72}IrNP^+$: 958.5032. Found 958.5033.

The following compounds are prepared by the same method with example 5.

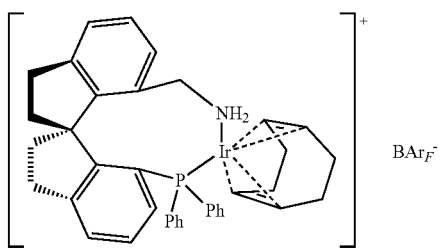

5b

It is croci solid. Yield percentage: 89%. Melting point: 192-194. $[\alpha]_D^{25}$ −167 (c 0.5, $CH_2Cl_2$). 1H NMR (400 MHz, $CDCl_3$) δ 7.99-7.91 (m, 1H), 7.77-7.65 (m, 8H), 7.60-7.50 (m, 6H), 7.50-7.27 (m, 11H), 6.85-6.67 (m, 2H), 4.73-4.63 (m, 1H), 4.07-3.96 (m, 1H), 3.81-3.72 (m, 1H), 3.63-3.44 (m, 3H), 3.32-3.23 (m, 1H), 3.04-2.92 (m, 2H), 2.87-2.51 (m, 3H), 2.50-2.36 (m, 1H), 2.21-2.12 (m, 3H), 2.10-1.95 (m, 3H), 1.94-1.79 (m, 1H), 1.66-1.57 (m, 1H), 1.57-1.52 (m, 2H), 1.46 (dd, J=9.0 and 5.1 Hz, 1H); $^{31}$P NMR (162 MHz, $CDCl_3$) δ 12.7 (s); $^{13}$C NMR (100 MHz, $CDCl_3$) δ 162.6, 162.1, 161.6, 161.1, 151.8, 146.8, 146.8, 146.6, 145.5, 135.6, 135.6, 135.5, 135.0, 133.8, 132.9, 132.4, 130.4, 130.1, 129.7, 129.6, 129.5, 129.2, 128.9, 128.7, 128.6, 128.4, 128.3, 128.0, 127.2, 127.0, 126.8, 126.0, 124.1, 123.8, 123.3, 120.6, 119.2, 117.6, 74.9, 73.1, 70.8, 63.5, 61.7, 61.4, 47.1, 39.6, 35.4, 33.0, 31.2, 30.5, 30.3, 28.5. HRMS (MALDI) calcd for $C_{38}H_{40}IrNP^+$: 734.2528. Found 734.2519.

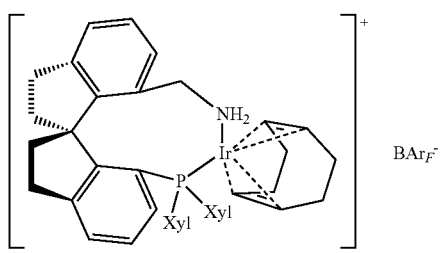

5c

It is croci solid. Yield percentage: 89%. Melting point: 196-198. $[\alpha]_D^{25}$ +152 (c 0.5, $CH_2Cl_2$). $^1$H NMR (400 MHz, $CDCl_3$) δ 7.96 (d, J=6.4 Hz, 1H), 7.74-7.71 (m, 8H), 7.67-7.45 (m, 6H), 7.43-7.41 (m, 1H), 7.37-7.27 (m, 3H), 7.26 (s, 1H), 7.17 (s, 1H), 7.09 (s, 1H), 6.93-6.85 (m, 2H), 4.67 (dd, J=13.2 and 8.2 Hz, 1H), 4.05-3.98 (m, 1H), 3.72-3.69 (m, 1H), 3.54-3.50 (m, 3H), 3.29-3.23 (m, 1H), 3.02-2.98 (m, 2H), 2.84-2.55 (m, 3H), 2.49-2.35 (m, 1H), 2.26 (s, 12H), 2.16 (s, 3H), 2.11-1.86 (m, 5H), 1.66-1.51 (m, 3H); $^{31}$P NMR (162 MHz, $CDCl_3$) δ 12.9 (s); $^{13}$C NMR (100 MHz, $CDCl_3$) δ 162.7, 162.2, 161.05, 151.6, 147.1, 146.3, 145.6, 139.4, 138.1, 135.0, 134.0, 133.3, 132.4, 132.0, 130.1, 129.9, 129.7, 129.4, 129.0, 127.9, 127.5, 126.8, 126.4, 126.1, 124.8, 124.4, 123.4, 120.6, 119.3, 117.6, 74.8, 72.2, 70.9, 68.9, 63.5, 61.0, 47.1, 39.5, 35.0, 32.8, 31.9, 31.1, 30.9, 30.1, 29.8, 28.9, 21.1. HRMS (MALDI) calcd for $C_{42}H_{48}IrNP^+$: 790.3154. Found 790.3148.

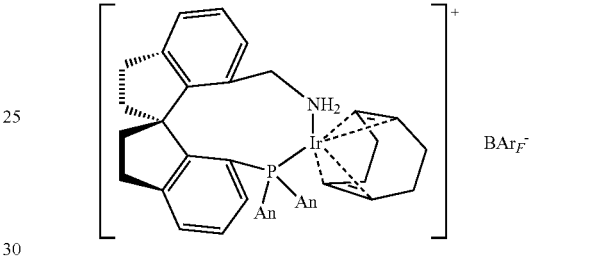

5d

It is croci solid. Yield percentage: 94%. Melting point: 120-122. $[\alpha]_D^{23}$ +121 (c 0.5, $CH_2Cl_2$). $^1$H NMR (400 MHz, $CDCl_3$) δ 7.93 (d, J=6.1 Hz, 1H), 7.71 (m, 9H), 7.58-7.37 (m, 7H), 7.36-7.26 (m, 4H), 6.99-6.77 (m, 5H), 3.84 (s, 3H), 3.82 (s, 3H), 3.52 (m, 3H), 3.28 (m, 1H), 2.99 (m, 2H), 2.82-2.65 (m, 2H), 2.62-2.51 (m, 1H), 2.50-2.28 (m, 1H), 2.14-1.87 (m, 4H), 1.71-1.39 (m, 10H); $^{31}$P NMR (162 MHz, $CDCl_3$) δ 10.3 (s); $^{13}$C NMR (100 MHz, $CDCl_3$) δ 162.7, 162.0, 161.5, 161.3, 161.1, 151.6, 151.5, 146.8, 146.7, 146.6, 145.4, 134.9, 133.6, 130.1, 129.4, 129.2, 128.8, 128.68, 127.9, 126.9, 126.0, 125.2, 124.9, 123.6, 123.3, 123.0, 120.6, 119.5, 117.5, 115.1, 113.9, 113.8, 74.2, 73.1, 70.5, 63.4, 61.4, 61.2, 55.3, 55.2, 47.1, 39.7 35.5, 32.9, 32.8, 31.9, 31.2, 30.7, 30.6, 30.3, 29.7, 29.4, 28.6, 28.6, 22.7. HRMS (MALDI) calcd for $C_{40}H_{44}IrNO_2P^+$: 794.2733. Found 794.2727.

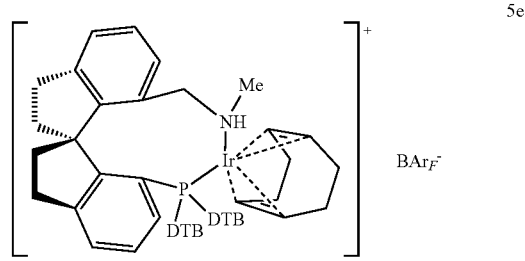

5e

It is croci solid. Yield percentage: 76%. Melting point: 210-212. $[\alpha]_D^{25}$ +104 (c 0.5, $CH_2Cl_2$). $^1$H NMR (400 MHz,) δ 7.93 (d, J=6.7 Hz, 1H), 7.74-7.71 (m, 9H), 7.61 (s, 1H), 7.56-7.38 (m, 8H), 7.36-7.27 (m, 2H), 7.04-6.92 (m, 1H), 6.31 (d, J=10.8 Hz, 1H), 6.11 (dd, J=7.0 and 3.8 Hz, 1H), 4.85 (dd, J=12.5 and 6.1 Hz, 1H), 4.61 (dd, J=9.4 and 4.8 Hz, 1H), 4.05 (dd, J=11.7 and 7.7 Hz, 1H), 3.82 (dt, J=17.8 and 9.3 Hz, 2H), 3.42-3.28 (m, 2H), 3.02 (dd, J=9.6 and 3.7 Hz, 2H), 2.79-2.59 (m, 2H), 2.31 (tdd, J=10.8 and 7.2 and 3.6 Hz, 1H), 2.21-1.97 (m, 6H), 1.90 (dd, J=16.4 and 10.0 Hz, 1H), 1.64-1.48 (m, 3H), 1.30 (m, 22H), 1.08 (s, 18H); $^{31}$P NMR (162 MHz, CDCl$_3$) δ 16.7 (s); $^{13}$C NMR (100 MHz, CDCl$_3$) δ 162.5, 162.0, 161.5, 161.0, 152.5, 151.8, 151.7, 151.6, 151.5, 149.8, 149.7, 148.5, 148.1, 146.7, 146.5, 146.5, 145.1, 144.1, 136.5, 134.8, 134.0, 132.1, 131.9, 131.4, 131.1, 131.1, 129.7, 129.3, 129.3, 129.0, 128.7, 128.6, 128.4, 128.3, 128.2, 128.1, 126.5, 126.4, 126.0, 126.0, 125.9, 124.0, 123.2, 122.0, 121.6, 120.5, 117.7, 117.4, 115.4, 112.6, 72.6, 71.8, 68.9, 63.6, 61.3, 61.0, 58.5, 39.3, 36.3, 35.1, 35.0, 34.8, 31.2, 31.0, 31.0, 30.9, 30.2, 29.7, 29.6, 29.2, 23.7, 22.8, 22.7, 22.4, 22.1, 21.9, 21.3, 21.0, 21.0, 20.9, 20.7, 20.4, 20.3, 20.1, 14.1. HRMS (MALDI) calcd for C$_{55}$H$_{74}$IrNP$^+$: 972.5188. Found 972.5193.

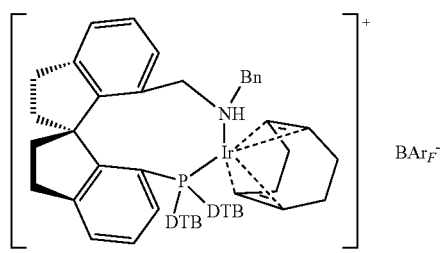

5f

It is croci solid. Yield percentage: 76%. Melting point: 210-212. $[\alpha]_D^{25}$ +76 (c 0.1, CH$_2$Cl$_2$). $^1$H NMR (400 MHz,) δ 7.95 (d, J=7.1 Hz, 1H), 7.89-7.79 (m, 1H), 7.77-7.56 (m, 12H), 7.51 (m, 3H), 7.36-7.15 (m, 8H), 7.00 (d, J=9.7 Hz, 1H), 6.37 (m, 2H), 6.10 (d, J=12.7 Hz, 1H), 4.39 (dd, J=12.5 and 5.9 Hz, 1H), 4.28-4.18 (m, 1H), 4.13-4.04 (m, 1H), 3.69-3.62 (m, 2H), 3.54-3.40 (m, 2H), 3.01-2.40 (m, 4H), 1.93-1.40 (m, 9H), 1.35 (s, 7H), 1.26 (d, J=6.5 Hz, 16H), 1.09 (d, J=17.9 Hz, 13H), 0.95-0.72 (m, 5H). $^{31}$P NMR (162 MHz, CDCl$_3$) δ 16.2 (s); $^{13}$C NMR (100 MHz, CDCl$_3$): δ 162.0, 161.5, 151.9, 147.0, 146.2, 145.2, 134.8, 134.3, 132.5, 132.2, 131.0, 129.7, 129.4, 129.0, 128.7, 128.3, 127.7, 126.8, 126.3, 125.9, 124.0, 123.2, 117.5, 72.1, 69.3, 63.6, 61.4, 55.1, 54.8, 38.4, 35.3, 35.0, 34.9, 31.9, 31.3, 31.2, 31.0, 30.9, 30.0, 29.7, 29.4, 22.7, 14.1. HRMS (MALDI) calcd for C$_{61}$H$_{78}$IrNP$^+$: 1048.5501. Found 1048.5502.

By replacing NaBAr$_F$ with sodium salt and silver salt containing different anion, various spiro benzyl amine-phosphine/iridium complexes containing different anions can be prepared at on site. Specific operation can be referred to example 10.

Example 6

Asymmetric Hydrogenation of (R)-Isoibuprofen

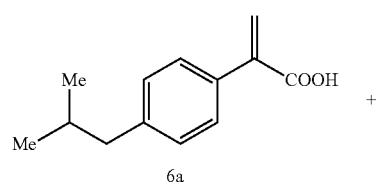

6a

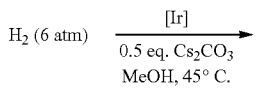

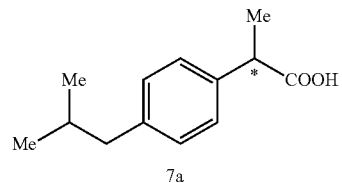

7a

The catalyst (0.0005 mmol) and 2-4-isobutyl-acrylic acid 6a (102 mg, 0.5 mmol) were weighed from glove box and transferred into the reaction inner tube containing a stir bar. The tube was sealed as a spare. Cesium carbonate (82 mg, 0.25 mmol) and methanol (2 mL) were added into the tube after fetching out the tube. The inner tube was placed in the hydrogenation reaction still. The original atmosphere was displaced with hydrogen atmosphere by inflating-deflating operation (3-5 times). The hydrogen pressure was ultimately set at 0.6 MPa. At the temperature of 45, the reaction was proceeded with stirring until the pressure stopped decreasing. After stopping stirring to release hydrogen and concentrating the system with rotary steaming, the pH value of the system was adjusted with 3 N hydrochloric acid until pH<3. The mixture was extracted by ether (10 mL 3). The organic phases merged together were washed by sodium chloride solution and dried by anhydrous sodium sulfate. The drying agent was removed by suction filtration. The target product 7a was obtained after solvent was removed by rotary steaming. Melting point: 53-55. $\{[\alpha]_D^{30}$ −52 (c 2.0, ethanol); $^1$H NMR (400 MHz, CDCl$_3$): δ 9.98 (brs, 1H, COOH), 7.24 (d, J=7.6 Hz, 2H, Ar—H), 7.12 (d, J=7.6 Hz, 2H, Ar—H), 3.73 (q, J=7.2 Hz, 1H, CH), 2.47 (d, J=7.2 Hz, 2H, CH$_2$), 1.86 (septet, J=6.8 Hz, 1H, CH), 1.52 (d, J=7.2 Hz, 3H, CH$_3$), 0.92 (d, J=6.4 Hz, 6H, CH$_3$)$\}$ The conversion rate was analyzed by $^1$H NMR and the ee value was analyzed by chiral GC after the product was transformed into corresponding methyl ester. The experimental results determined are listed in Table 1:

TABLE 1

Experimental results of asymmetric hydrogenation of 2-4-isobutyl-acrylic acid treated by various iridium catalysts

| [Ir] | duration | percent convertion (%) | ee value (%) |
| --- | --- | --- | --- |
| (S)-5a | 10 min | 100 | 98 (R) |
| (R)-5b | 2 h | 100 | 92 (S) |
| (S)-5c | 1 h | 100 | 94 (R) |
| (S)-5e | 18 h | 44 | 98 (R) |
| (S)-5f | 18 h | 70 | 92 (R) |

Example 7

Asymmetric Hydrogenation of (R)-Isoibuprofen at Various Temperature

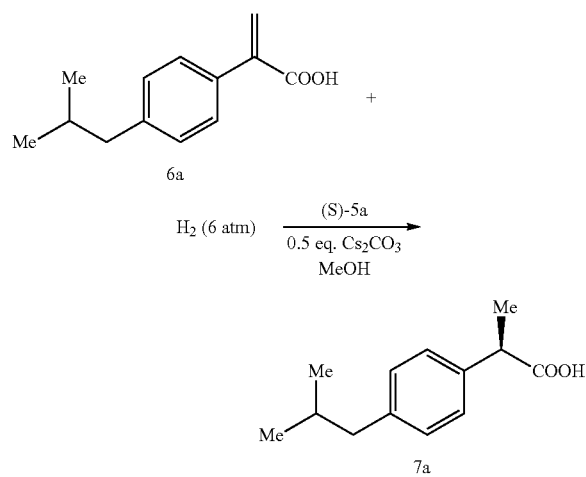

The catalyst (S)-5a (0.9 mg, 0.0005 mmol) and 2-4-isobutyl-acrylic acid 6a (102 mg, 0.5 mmol) were weighed from glove box and transferred into the reaction inner tube containing a stir bar. The tube was sealed as a spare. Cesium carbonate (82 mg, 0.25 mmol) and methanol (2 mL) were added into the tube after fetching out the tube. The inner tube was placed in the hydrogenation reaction still. The original atmosphere was displaced with hydrogen atmosphere by inflating-deflating operation (3-5 times). The hydrogen pressure was ultimately set at 0.6 MPa. At the temperature of 45, the reaction was proceeded with stirring until the pressure stopped decreasing. After stopping stirring to release hydrogen and concentrating the system with rotary steaming, the pH value of the system was adjusted with 3 N hydrochloric acid until pH<3. The mixture was extracted by ether (10 mL 3). The organic phases merged together were washed by sodium chloride solution and dried by anhydrous sodium sulfate. The drying agent was removed by suction filtration. The target product (R) 7a was obtained after solvent was removed by rotary steaming. The conversion rate was analyzed by $^1$H NMR and the ee value was analyzed by chiral GC after the product was transformed into corresponding methyl ester. The experimental results determined are listed in Table 2:

TABLE 2

Experimental results of asymmetric hydrogenation of 2-4-isobutyl-acrylic acid at various temperatures

| temperature (° C.) | duration (min) | percent convertion (%) | ee value (%) |
|---|---|---|---|
| 25 | 40 | 100 | 98 |
| 45 | 10 | 100 | 98 |
| 60 | 5 | 100 | 98 |

Example 8

Asymmetric Hydrogenation of (R)-Isoibuprofen Under Various Pressures

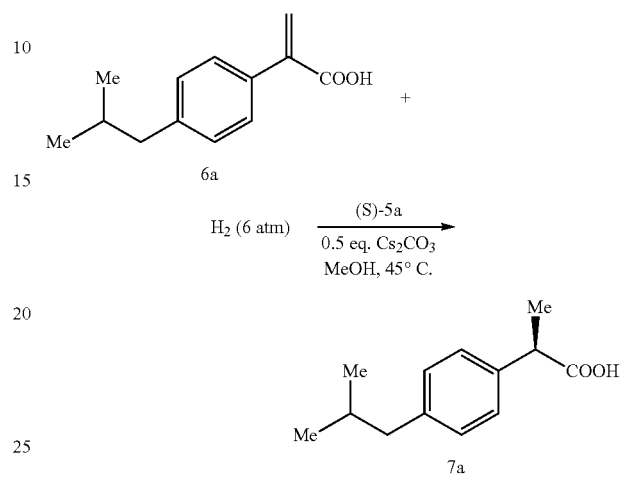

The catalyst (S)-5a (0.9 mg, 0.0005 mmol) and 2-4-isobutyl-acrylic acid 6a (102 mg, 0.5 mmol) were weighed from glove box and transferred into the reaction inner tube containing a stir bar. The tube was sealed as a spare. Cesium carbonate (82 mg, 0.25 mmol) and methanol (2 mL) were added into the tube after fetching out the tube. The inner tube was placed in the hydrogenation reaction still. The original atmosphere was displaced with hydrogen atmosphere by inflating-deflating operation (3-5 times). The hydrogen pressure was ultimately set at 0.6 MPa. At the temperature of 45, the reaction was proceeded with stirring until the pressure stopped decreasing. After stopping stirring to release hydrogen and concentrating the system with rotary steaming, the pH value of the system was adjusted with 3 N hydrochloric acid until pH<3. The mixture was extracted by ether (10 mL 3). The organic phases merged together were washed by sodium chloride solution and dried by anhydrous sodium sulfate. The drying agent was removed by suction filtration. The target product (R) 7a was obtained after solvent was removed by rotary steaming. The conversion rate was analyzed by $^1$H NMR and the ee value was analyzed by chiral GC after the product was transformed into corresponding methyl ester. The experimental results determined are listed in Table 3:

TABLE 3

Experimental results of asymmetric hydrogenation of 2-4-isobutyl-acrylic acid at various pressures

| Hydrogen pressure (MPa) | duration | percent convertion (%) | ee value (%) |
|---|---|---|---|
| Normal pressure | 4 h | 100 | 99 |
| 0.6 | 10 min | 100 | 98 |
| 7 | 5 min | 100 | 91 |

Example 9

Asymmetric Hydrogenation of (R)-Isoibuprofen on Adding Various Additives

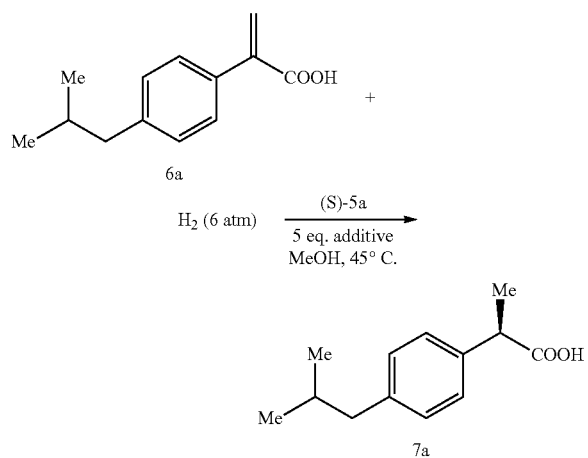

The catalyst (S)-5a (0.9 mg, 0.0005 mmol) and 2-4-isobutyl-acrylic acid 6a (102 mg, 0.5 mmol) were weighed from glove box and transferred into the reaction inner tube containing a stir bar. The tube was sealed as a spare. Cesium carbonate (82 mg, 0.25 mmol) and methanol (2 mL) were added into the tube after fetching out the tube. The inner tube was placed in the hydrogenation reaction still. The original atmosphere was displaced with hydrogen atmosphere by inflating-deflating operation (3-5 times). The hydrogen pressure was ultimately set at 0.6 MPa. At the temperature of 45, the reaction was proceeded with stirring until the pressure stopped decreasing. After stopping stirring to release hydrogen and concentrating the system with rotary steaming, the pH value of the system was adjusted with 3 N hydrochloric acid until pH<3. The mixture was extracted by ether (10 mL 3). The organic phases merged together were washed by sodium chloride solution and dried by anhydrous sodium sulfate. The drying agent was removed by suction filtration. The target product (R) 7a was obtained after solvent was removed by rotary steaming. The conversion rate was analyzed by $^1$H NMR and the ee value was analyzed by chiral GC after the product was transformed into corresponding methyl ester. The experimental results determined are listed in Table 4:

TABLE 4

Experimental results of asymmetric hydrogenation of 2-4-isobutyl-acrylic acid on adding various additives

| additive | duration | percent convertion (%) | ee value (%) |
|---|---|---|---|
| $Cs_2CO_3$ | 10 min | 100 | 98 |
| $Na_2CO_3$ | 30 min | 100 | 98 |
| $K_2CO_3$ | 30 min | 100 | 98 |
| $^tBuOK$ | 30 min | 100 | 98 |
| MeONa | 20 min | 100 | 98 |
| $Et_3N$ | 15 min | 100 | 98 |
| $^tBuNH_2$ | 15 min | 100 | 98 |
| N/A | 21 h | 25 | 91 |

Example 10

Synthesis of (R)-Isoibuprofen Catalyzed by Catalysts with Various Anions

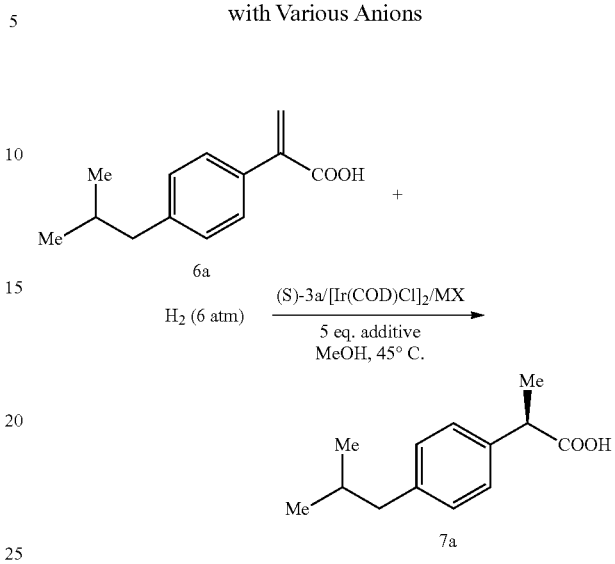

Spirobenzylamine-phosphine (S)-3a (0.001 mmol), [Ir(COD)Cl]$_2$ (0.00055 mmol) and MX (0.0012 mmol) was weighed from glove box and transferred into the reaction inner tube containing a stir bar. The complexation was proceeded with stirring for 2 hours after adding 1 mL anhydrous dichloromethane. The inner tube, added with 2-4-isobutyl-acrylic acid 6a (204 mg, 1 mmol), cesium carbonate (164 mg, 0.5 mmol) and methanol (4 mL) after complexation, was placed in the hydrogenation reaction still. The original atmosphere was displaced with hydrogen atmosphere by inflating-deflating operation (3-5 times). The hydrogen pressure was ultimately set at 0.6 MPa. At the temperature of 45, the reaction was proceeded with stirring until the pressure stopped decreasing. After stopping stirring to release hydrogen and concentrating the system with rotary steaming, the pH value of the system was adjusted with 3 N hydrochloric acid until pH<3. The mixture was extracted by ether (10 mL 3). The organic phases merged together were washed by sodium chloride solution and dried by anhydrous sodium sulfate. The drying agent was removed by suction filtration. The target product (R) 7a was obtained after solvent was removed by rotary steaming. The conversion rate was analyzed by $^1$H NMR and the ee value was analyzed by chiral GC after the product was transformed into corresponding methyl ester. The experimental results determined are listed in Table 5:

TABLE 5

Experimental results of asymmetric hydrogenation of 2-4-isobutyl-acrylic acid treated by catalysts with various anions.

| MX | duration | percent convertion (%) | ee value (%) |
|---|---|---|---|
| N/A | 40 min | 100 | 98 |
| $NaBAr_F$ | 10 min | 100 | 98 |
| $NaClO_4 \cdot H_2O$ | 30 min | 100 | 98 |
| AgOTf | 20 min | 100 | 98 |
| $AgPF_6$ | 15 min | 100 | 98 |
| $AgBF_4$ | 20 min | 100 | 98 |

Example 11

Synthesis of (R)-Isoibuprofen with Low Catalyst Dosage

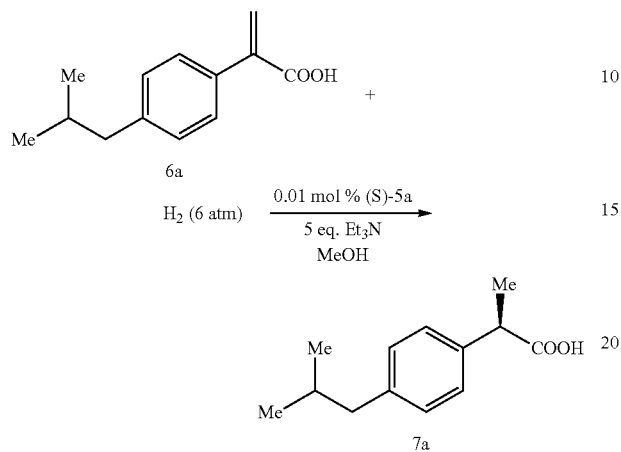

The catalyst (S)-5a (1.1 mg, 0.0006 mmol) was weighed from glove box and transferred into the reaction inner tube containing a stir bar. The catalyst was completely dissolved by stirring after adding 12 mL methanol. 10 mL of catalyst solution was removed before triethylamine (70 μL), methanol (2 mL) and 2-4-isobutyl-acrylic acid 6a (204 mg, 1 mmol) was added to the remaining 2 mL solution. The inner tube was placed in the hydrogenation reaction still. The original atmosphere was displaced with hydrogen atmosphere by inflating-deflating operation (3-5 times). At the temperature of 60, the reaction was proceeded with stirring until the pressure stopped decreasing. After stopping stirring to release hydrogen and concentrating the system with rotary steaming, the pH value of the system was adjusted with 3 N hydrochloric acid until pH<3. The mixture was extracted by ether (10 mL 3). The organic phases merged together were washed by sodium chloride solution and dried by anhydrous sodium sulfate. The drying agent was removed by suction filtration. The target product (R) 7a which was white solid was obtained after solvent was removed by rotary steaming. The conversion rate was 100% and the yield was 98% after analyzed by $^1$H NMR. After the product was transformed into corresponding methyl ester, the ee value was 97% after analyzed by chiral GC.

Example 12

Hydrogenation of Alpha-Substituted Acrylic Acid at the Hydrogen Pressure of 0.6 MPa

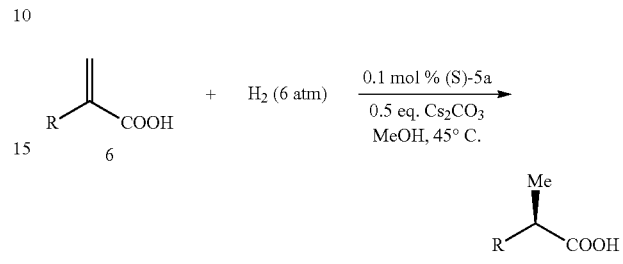

The catalyst (S)-5a (0.9 mg, 0.0005 mmol), alpha-substituted acrylic acid 6 (0.5 mmol) and cesium carbonate (82 mg, 0.25 mmol) were weighed from glove box and transferred into the reaction inner tube containing a stir bar. The tube was sealed as a spare. Methanol (2 mL) was injected into the tube with syringe after fetching out the tube. The inner tube was placed in the hydrogenation reaction still. The original atmosphere was displaced with hydrogen atmosphere by inflating-deflating operation (3-5 times). The hydrogen pressure was ultimately set at 0.6 MPa. At the temperature of 45, the reaction was proceeded with stirring until the pressure stopped decreasing. After stopping stirring to release hydrogen and concentrating the system with rotary steaming, the pH value of the system was adjusted with 3 N hydrochloric acid until pH<3. The mixture was extracted by ether (10 mL 3). The organic phases merged together were washed by sodium chloride solution and dried by anhydrous sodium sulfate. The drying agent was removed by suction filtration. The target product (R) 7 was obtained after solvent was removed by rotary steaming. The conversion rate was analyzed by $^1$H NMR proving that all of the reactions were converted completely. The ee value was analyzed by chiral GC, chiral HPLC or chiral SFC after the product was transformed into corresponding methyl ester. The experimental results determined are listed in Table 6.

TABLE 6

Experimental results of asymmetric hydrogenation of alpha-substituted acrylic acid at the hydrogen pressure of 0.6 MPa

| substrate 6 | substrate 7 | duration | Yield (%) | ee value (%) |
|---|---|---|---|---|
| (phenyl acrylic acid) | (phenyl propionic acid) | 15 min | 97 | 98 (R) |
| (4-MeO-phenyl acrylic acid) | (4-MeO-phenyl propionic acid) | 15 min | 98 | 98 (R) |

TABLE 6-continued

Experimental results of asymmetric hydrogenation of alpha-substituted acrylic acid at the hydrogen pressure of 0.6 MPa

| substrate 6 | substrate 7 | duration | Yield (%) | ee value (%) |
|---|---|---|---|---|
| 4-Cl-C6H4-C(=CH2)-COOH | (R)-4-Cl-C6H4-CH(CH3)-COOH | 30 min | 98 | 97 (R) |
| 2-F-4-Ph-C6H3-C(=CH2)-COOH | (R)-2-F-4-Ph-C6H3-CH(CH3)-COOH | 15 min | 99 | 96 (R) |
| 6-MeO-naphthyl-C(=CH2)-COOH | (R)-6-MeO-naphthyl-CH(CH3)-COOH | 15 min | 99 | 97 (R) |
| PhCH2-C(=CH2)-COOH | (R)-PhCH2-CH(CH3)-COOH | 15 min | 99 | 98 (R) |
| PhCH2CH2-C(=CH2)-COOH | (R)-PhCH2CH2-CH(CH3)-COOH | 1 h | 99 | 92 (R) |
| iPr-C(=CH2)-COOH | (R)-iPr-CH(CH3)-COOH | 25 min | 97 | 96 (R) |
| n-Hex-C(=CH2)-COOH | (R)-n-Hex-CH(CH3)-COOH | 30 min | 97 | 94 (R) |
| MeOOC-CH2-C(=CH2)-COOH | (R)-MeOOC-CH2-CH(CH3)-COOH | 15 min | 99 | 95 (R) |
| PhO-CH2-C(=CH2)-COOH | (R)-PhO-CH2-CH(CH3)-COOH | 15 min | 94 | 96 (R) |
| EtO-CH2-C(=CH2)-COOH | (R)-EtO-CH2-CH(CH3)-COOH | 15 min | 98 | 95 (R) |

Example 13

Hydrogenation of Alpha-Substituted Acrylic Acid at Normal Pressure

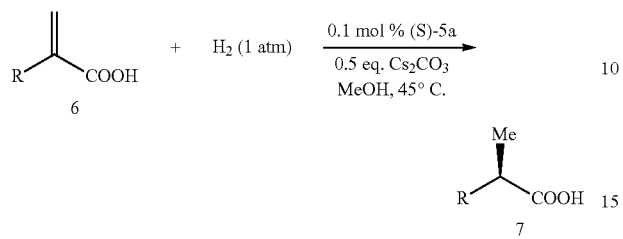

The catalyst (S)-5a (0.9 mg, 0.0005 mmol), alpha-substituted acrylic acid 6 (0.5 mmol) and cesium carbonate (82 mg, 0.25 mmol) were weighed from glove box and transferred into the Schlenk reaction tube containing a stir bar. The tube was sealed as a spare. Methanol (2 mL) was injected into the tube with syringe after fetching out the tube. The original atmosphere was displaced with hydrogen atmosphere at vacuum lines. The hydrogenation was proceeded at normal pressure and was confirm by TLC to be completely converted. After stopping stirring, the system was concentrated with rotary steaming and the pH value of the system was adjusted with 3 N hydrochloric acid until pH<3. The mixture was extracted by ether (10 mL 3). The organic phases merged together were washed by sodium chloride solution and dried by anhydrous sodium sulfate. The drying agent was removed by suction filtration. The target product (R) 7 was obtained after solvent was removed by rotary steaming. The conversion rate was analyzed by $^1$H NMR proving that all of the reactions were converted completely. The ee value was analyzed by chiral GC, chiral HPLC or chiral SFC after the product was transformed into corresponding methyl ester. The experimental results determined are listed in Table 7.

TABLE 6

Experimental results of asymmetric hydrogenation of alpha-substituted acrylic acid at normal pressure

| substrate 6 | substrate 7 | duration | Yield (%) | ee value (%) |
|---|---|---|---|---|
| 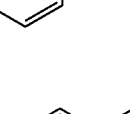 | 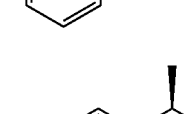 | 4 h | 95 | 98 (R) |
| 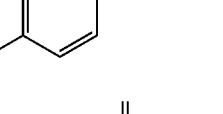 | 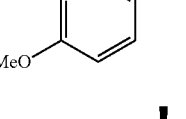 | 4 h | 96 | 99 (R) |
| 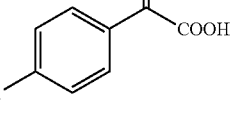 | 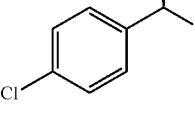 | 8 h | 96 | 98 (R) |
| 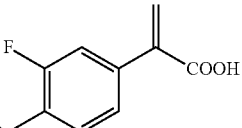 | 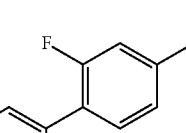 | 4 h | 98 | 97 (R) |
|  | 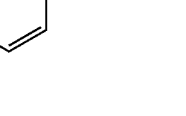 | 4 h | 98 | 98 (R) |
| 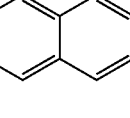 | 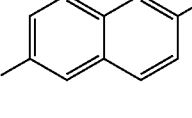 | 4 h | 98 | 98 (R) |

TABLE 6-continued

Experimental results of asymmetric hydrogenation of alpha-substituted acrylic acid at normal pressure

| substrate 6 | substrate 7 | duration | Yield (%) | ee value (%) |
|---|---|---|---|---|
| Ph-CH₂-CH₂-C(=CH₂)-COOH | Ph-CH₂-CH₂-CH(·)-COOH | 4 h | 98 | 97 (R) |
| $^i$Pr-C(=CH₂)-COOH | $^i$Pr-CH(·)-COOH | 4 h | 95 | 96 (R)$^a$ |
| n-Hex-C(=CH₂)-COOH | n-Hex-CH(·)-COOH | 4 h | 96 | 98 (R)$^a$ |
| MeOOC-CH₂-C(=CH₂)-COOH | MeOOC-CH₂-CH(·)-COOH | 4 h | 96 | 97 (R) |
| PhO-CH₂-C(=CH₂)-COOH | PhO-CH₂-CH(·)-COOH | 4 h | 98 | 96 (R) |
| EtO-CH₂-C(=CH₂)-COOH | EtO-CH₂-CH(·)-COOH | 4 h | 97 | 98 (R) |

Since the spirobenzylamine-phosphine, preparation methods and uses thereof, suggested by the present invention, have been described by particular examples, relevant technicists are obviously incapable of adjusting and modifying spirobenzylamine-phosphine, preparation methods and uses thereof described in this article without referring to the content, spirits and scope of the present invention when attempting to realize this technique. It should be particularly noted that all of the similar replacement and modification which is obvious to the technicists in this field are treated as inclusion of the content, spirits and scope of the present invention.

What is claimed is:

1. A compound of spirobenzylamine-phosphine of the following structure formula:

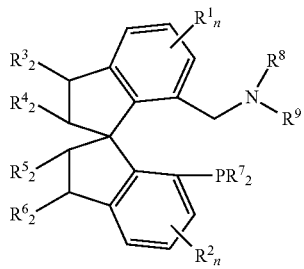

wherein n=0~3; $R^1$ and $R^2$ represent $C_1$-$C_8$ alkyl, halogenated alkyl, $C_1$-$C_8$ alkoxy, $C_2$-$C_8$ acyloxy, $C_1$-$C_8$ acyl, $C_2$-$C_8$ ester group, ($C_1$-$C_8$ acyl) azyl, ($C_1$-$C_8$ alkyl)diamino group, halogen, phenyl, substituted phenyl, naphthyl, substituted naphthyl, fruyl, thienyl, and fused aliphatic ring or fused aromatic ring when n≥2; $R^1$ and $R^2$ can be either identical or not;

$R^3$, $R^4$, $R^5$ and $R^6$ represent H, $C_1$-$C_8$ alkyl, halogenated alkyl, $C_1$-$C_8$ alkoxy, $C_2$-$C_8$ acyloxy, $C_1$-$C_8$ acyl, $C^2$-$C_8$ ester group, (Cj-Cs acyl) azyl, (CpCg alkyl)diamino group, halogen, phenyl, substituted phenyl, naphthyl, substituted naphthyl, fruyl and thienyl; $R^3$-$R^4$, $R^5$-$R^6$ may be fused aliphatic ring or aromatic ring, $R^3$, $R^4$, $R^5$ and $R^6$ can be either identical or not;

$R^7$ represents $C_1$-$C_8$ alkyl, phenyl, substituted phenyl, naphthyl, substituted naphthyl, fruyl, and thienyl;

$R^8$ and $R^9$ represent H, $C_1$-$C_8$ alkyl, benzyl, substituted benzyl, phenyl, substituted phenyl, naphthyl, substituted naphthyl, fruyl and thienyl; $R^8$ and $R^9$ can be either identical or not; in the substituted phenyl or naphthyl described above, the substituent groups may be one or more of $C_1$-$C_8$ alkyl, $C_1$-$C_8$ alkoxy, hydroxyl, $C_1$-$C_8$ acyloxy, halogen, amino, ($C_1$-$C_8$ acyl) azyl, ($C_1$-$C_8$ alkyl)diamino group, $C_1$-$C_8$ acyl and $C_1$-$C_8$ ester group; the number of substituents ranges from 0 to 5.

2. The compound of spirobenzylamine-phosphine according to claim 1, wherein, the $C_1$-$C_8$ alkyl is selected from the group consisting of methyl, ethyl, propyl, isopropyl, butyl, isobutyl sec-butyl, tert-butyl, pentyl, isopentyl, neopentyl, sec-pentyl, tert-pentyl, hexyl, isohexyl, neohexyl, sec-hexyl, tert-hexyl, heptyl, isoheptyl, neoheptyl, sec-heptyl, tert-heptyl, octyl, isooctyl, neooctyl, sec-octyl, and tert-octyl;

the $C_1$-$C_8$ alkoxy is selected from the group consisting of methoxy, ethoxy, n-propoxy, isopropoxy, n-butoxy, isobutoxy, sec-butoxy, tert-butoxy, n-pentyloxy, isopentyl, neopentyl, sec-pentyloxy, tert-pentyloxy, n-hexyloxy, isohexyloxy, neohexyloxy, sec-hexyloxy, tert-hexyloxy, n-lieptyloxy, isoheptyloxy, neoheptyloxy, sec-heptyloxy, tert-heptyloxy, n-octyloxy, iso-octyloxy, neooctyloxy, sec-octyloxy, and a tert-octyloxy;

the $C_1$-$C_8$ acyl is selected from the group consisting of formyl, acetyl, propionyl, n-butyryl, isobutyryl, n-valeryl, isovaleryl, sec-valeryl, pivaloyl, n-hexanoyl, isohexanoyl, neohexanoyl, sec-hexanoyl n-heptanoyl, isoheptanoyl, neoheptanoyl, sec-heptanoyl, n-caprylyl, isoeaprylyl, neocaprylyl, sec-caprylyl, 1-cyclopropyformyl, 1-cyclobutylformyl, 1-cyclopentylformyl, 1-cyclohexylformyl, and 1-cycloheptylformyl;

the $C_2$-$C_8$ acyloxy is selected from the group consisting of acetoxy, propionyloxy, n-butyryloxy, isobutyryloxy, n-valeryloxy, isovaleryloxy, neovaleryloxy sec-valeryloxy, n-hexanoyloxy, isohexanoyloxy, neoliexanoyloxy, sec-hexanoyloxy, n-heptanoyloxy, isoheptanoyloxy, neoheptanoyloxy, sec-heptanoyloxy, n-octanoyloxy, isooctanoyloxy, neooctanoyloxy, sec-octanoyloxy, 1-cyclopropylformyloxy, 1-cyclobutyl formyloxy, 1-cyclopentylformyloxy, 1-cyclohexylformyloxy, and 1-cycloheptylformyloxy;

the $C_2$-$C_8$ ester group is selected from the group consisting of methoxycarbonyl, ethoxycarbonyl, propoxycarbonyl, isopropoxycarbonyl, butyloxycarbonyl, isobutyloxycarbonyl, n-pentyloxycarbonyl, isopentyloxycarbonyl, neopentyoloxycarbonyl, sec-pentyloxycarbonyl, tert-pentyloxycarbonyl, cyclopentyloxycarbonyl, n-hexyloxycarbonyl, isohexyloxycarbonyl, neohexyloxycarbonyl, sec-hexyloxycarbonyl, tert-hexyloxycarbonyl, cyclohexyloxycarbonyl, n-heptyloxycarbonyl, isoheptyloxycarbonyl, neoheptyloxycarbonyl, sec-heptyloxycarbonyl, tert-heptyloxycarbonyl, and cycloheptyloxycarbonyl;

the halogenated alkyl is selected from the group consisting of fluoroalkyl, chloroalkyl, bromoalkyl, and iodoalkyl.

3. The compound of spirobenzylamine-phosphine according to claim 1, selected from the group consisting of a raceme, dextroisomer, laevoisomer with the same chemical structure general formula but different stereochemical structure and optical activity.

4. The compound of spirobenzylamine-phosphine according to claim 1, wherein, the spirobenzylamine-phosphine is:
7-aminomethyl-7'-bis(3,5-di-tert-butylphenyl)phosphino-1,1'-spirobiinedane,
7-aminomethyl-7'diphenylphosphino-1,1'-spirobiinedane,
7-aminomethyl-7'-bis(4-methylphenyl)phosphino-1,1'-spirobiinedane,
7-aminomethyl-7'-bis(4-methoxylphenyl)phosphino-1,1'-spirobiinedane,
7-aminomethyl-7'-bis(3,5-dimethylphenyl)phosphino-1,1'-spirobiinedane,
N-methyl-7-aminomethyl-7'-bis(3,5-di-tert-butylphenyl)phosphino-1,1'spirobiinedane, or
N-benzyl-7-aminomethyl-7'-bis(3,5-di-tert-butylphenyl)phosphino-1,1'spirobiinediane.

5. A preparation method of the spirobenzylamine-phosphine according to claim 1, comprising the steps of:
subjecting 7-trifluoromesyloxy-7'-diarylphosphino-1,1'-spiro-dihydroindene 1 as the raw material to a palladium-catalyzed cyanation reaction to prepare intermediate 2

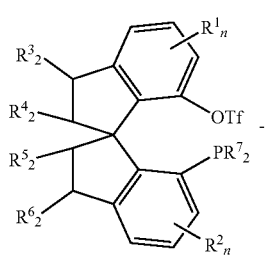

1

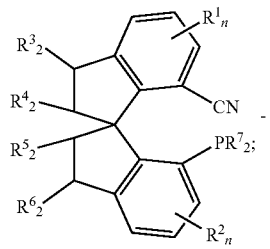

2 converting the intermediate 2 to spirobenzylamine-phospine 3

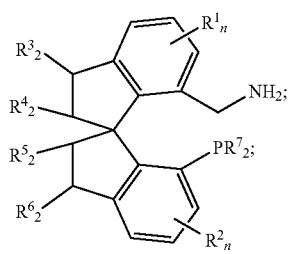

3 subjecting the spirobenzylamine-phosphine to a substitution reaction to prepare spirobenzylamine-phosphine 4,

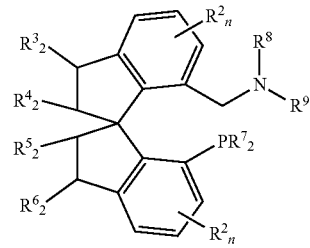

4 wherein R8 and R9 are not both H.

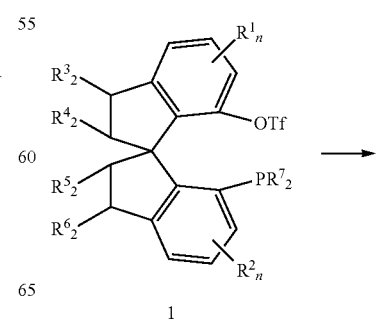

1

33
-continued
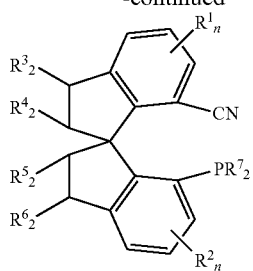
2
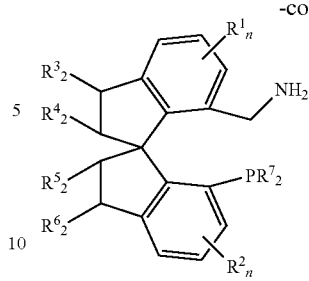
3
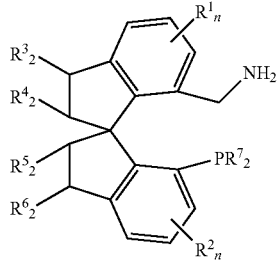
3
34
-continued
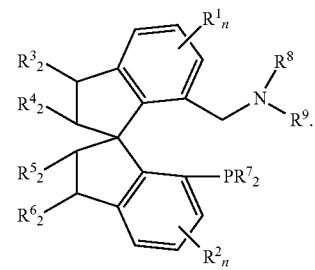
4
R⁸, R⁹ ≠ H
* * * * *